US012727864B2

(12) United States Patent
Shalon

(10) Patent No.: US 12,727,864 B2
(45) Date of Patent: Sep. 8, 2026

(54) DEVICES AND METHODS FOR COLLECTING GASTROINTESTINAL SAMPLES

(71) Applicant: ENVIVO BIO INC, San Carlos, CA (US)

(72) Inventor: Tidhar Dari Shalon, Los Altos Hills, CA (US)

(73) Assignee: Envivo Bio Inc, San Carlos, CA (US)

( * ) Notice: Subject to any disclaimer, the term of this patent is extended or adjusted under 35 U.S.C. 154(b) by 1249 days.

(21) Appl. No.: 17/437,440

(22) PCT Filed: Jan. 31, 2020

(86) PCT No.: PCT/US2020/016280
§ 371 (c)(1),
(2) Date: Sep. 9, 2021

(87) PCT Pub. No.: WO2020/185326
PCT Pub. Date: Sep. 17, 2020

(65) Prior Publication Data

US 2022/0175351 A1 Jun. 9, 2022

Related U.S. Application Data

(60) Provisional application No. 62/817,476, filed on Mar. 12, 2019, provisional application No. 62/870,723,
(Continued)

(51) Int. Cl.
*A61B 10/00* (2006.01)
*C12Q 1/6886* (2018.01)
*C12Q 1/70* (2006.01)

(52) U.S. Cl.
CPC ........ *A61B 10/0045* (2013.01); *C12Q 1/6886* (2013.01); *C12Q 1/70* (2013.01);
(Continued)

(58) Field of Classification Search
CPC ........ A61B 10/0045; A61B 2010/0061; A61B 2010/0208; C12Q 1/6886; C12Q 1/70; C12Q 2600/158
See application file for complete search history.

(56) References Cited

U.S. PATENT DOCUMENTS 2,508,690 A 5/1950 Schmerl
2,907,326 A 10/1959 Horace
(Continued)

FOREIGN PATENT DOCUMENTS

CN 105050500 A 11/2015
CN 212346576 U 1/2021
(Continued)

OTHER PUBLICATIONS

International Search Report and Written Opinion issued in PCT Application No. PCT/US2020/016280, mailed May 11, 2020, in 8 pages.

*Primary Examiner* — Abid A Mustansir
(74) *Attorney, Agent, or Firm* — Knobbe, Martens, Olson & Bear, LLP

(57) ABSTRACT

Disclosed is a method of identifying and/or localizing a pathology comprising sequentially collecting liquid samples from regions of GI tract into a single tube to form a linear array of samples within the single tube, localizing each of the samples to a specific region of the GI tract, and characterizing cells and/or biomolecules in each sample and associating the cells and/or the biomolecules with a pathology to a specific region of the GI tract to thereby identify and/or localize the pathology. Another method of localizing the pathology comprises sequentially collecting liquid samples from regions of a GI tract into a single tube to form a linear array of samples within the single tube, characterizing cells and/or biomolecules in each liquid sample, and identifying a GI region where the cells and/or the biomol-
(Continued)

ecules of interest first appear, thereby localizing the pathology to a specific region of the GI tract.

19 Claims, 9 Drawing Sheets

Related U.S. Application Data filed on Jul. 4, 2019, provisional application No. 62/826,845, filed on Mar. 29, 2019, provisional application No. 62/902,908, filed on Sep. 19, 2019.

(52) U.S. Cl.
CPC ................ *A61B 2010/0061* (2013.01); *C12Q 2600/158* (2013.01)

(56) References Cited

U.S. PATENT DOCUMENTS

| | | | | |
|---|---|---|---|---|
| 3,066,672 | A | 12/1962 | Crosby, Jr. et al. | |
| 3,315,660 | A | 4/1967 | Abella | |
| 3,485,235 | A | 12/1969 | Felson | |
| 3,528,429 | A * | 9/1970 | Beal | A61B 10/02 600/572 |
| 3,683,890 | A | 8/1972 | Beal | |
| 4,186,730 | A | 2/1980 | Bucalo | |
| 4,187,860 | A | 2/1980 | Villari | |
| 4,481,952 | A | 11/1984 | Pawelec | |
| 4,643,192 | A | 2/1987 | Fiddian-Green | |
| 4,685,472 | A | 8/1987 | Muto | |
| 4,735,214 | A | 4/1988 | Berman | |
| 5,479,923 | A | 1/1996 | Rantala | |
| 5,611,787 | A | 3/1997 | Demeter et al. | |
| 5,738,110 | A | 4/1998 | Beal et al. | |
| 5,971,942 | A | 10/1999 | Gu et al. | |
| 6,149,607 | A | 11/2000 | Simpson et al. | |
| 7,037,275 | B1 | 5/2006 | Marshall et al. | |
| 11,766,249 | B2 | 9/2023 | Shalon | |
| 12,096,920 | B1 | 9/2024 | Shalon | |
| 12,349,873 | B2 | 7/2025 | Shalon | |
| 12,564,389 | B2 | 3/2026 | Shalon | |
| 2004/0039350 | A1 | 2/2004 | McKittrick | |
| 2004/0097834 | A1 | 5/2004 | Stoltz | |
| 2006/0024201 | A1 | 2/2006 | Bell | |
| 2007/0161928 | A1 | 7/2007 | Sprenkels et al. | |
| 2007/0173738 | A1 | 7/2007 | Stoltz | |
| 2008/0208077 | A1 | 8/2008 | Iddan et al. | |
| 2009/0216082 | A1 | 8/2009 | Rabinovitz | |
| 2009/0216085 | A1 | 8/2009 | Rabinovitz | |
| 2011/0060189 | A1 | 3/2011 | Belson | |
| 2011/0208011 | A1 | 8/2011 | Ben-Horin | |
| 2014/0303461 | A1 | 10/2014 | Callaghan et al. | |
| 2015/0064241 | A1 | 3/2015 | Conrad | |
| 2016/0038086 | A1 | 2/2016 | Wrigglesworth et al. | |
| 2017/0296092 | A1* | 10/2017 | Jones | A61B 5/065 |
| 2018/0164221 | A1* | 6/2018 | Singh | A61K 49/0058 |
| 2019/0287657 | A1 | 9/2019 | Holmes et al. | |
| 2020/0138416 | A1 | 5/2020 | Shalon | |
| 2020/0146541 | A1* | 5/2020 | Yangdai | A61B 34/73 |
| 2020/0323422 | A1 | 10/2020 | Duan | |
| 2023/0389902 | A1 | 12/2023 | Shalon | |
| 2024/0008858 | A1 | 1/2024 | Shalon | |
| 2024/0398394 | A1 | 12/2024 | Shalon | |

FOREIGN PATENT DOCUMENTS

| | | |
|---|---|---|
| JP | S-5376584 | 7/1978 |
| JP | H05-228128 | 9/1993 |
| WO | WO 79/00811 | 10/1979 |
| WO | WO 88/09162 | 12/1988 |
| WO | WO 2005/046485 | 5/2005 |
| WO | WO 2013/120184 | 8/2013 |
| WO | WO 2014/140334 | 9/2014 |
| WO | WO 2017/211872 A1 | 12/2017 |
| WO | 2018183941 A2 | 10/2018 |
| WO | 2018213729 A1 | 11/2018 |
| WO | WO 2020/185326 A1 | 9/2020 |
| WO | WO 2022/109425 A1 | 5/2022 |

* cited by examiner

DEVICES AND METHODS FOR COLLECTING GASTROINTESTINAL SAMPLES

CROSS REFERENCE TO RELATED APPLICATIONS

This application is a national stage application of the Patent Cooperation Treaty (PCT) international application titled "Devices And Methods For Collecting Gastrointestinal Samples", international application number PCT/US2020/016280, filed in the United States Patent and Trademark Office on Jan. 31, 2020, which claims priority to and the benefit of the provisional patent application titled "Devices And Methods For Collecting Gastrointestinal Samples", application No. 62/817,476, filed in the United States Patent and Trademark Office on 12 Mar. 2019, "Devices And Methods For Collecting Gastrointestinal Samples", application No. 62/826,845, filed in the United States Patent and Trademark Office on 29 Mar. 2019, "Devices And Methods For Collecting Gastrointestinal Samples", application No. 62/870,723, filed in the United States Patent and Trademark Office on 4 Jul. 2019, and "Devices And Methods For Collecting Gastrointestinal Samples", application No. 62/902,908, filed in the United States Patent and Trademark Office on 19 Sep. 2019.

All publications and patent applications mentioned in this specification are herein incorporated by reference in their entirety to the same extent as if each individual publication or patent application was specifically and individually indicated to be incorporated by reference.

FIELD OF THE INVENTION

This application relates to the field of gastrointestinal diagnosis and treatment.

BACKGROUND

It has recently been recognized that mammalian gastrointestinal (GI) tract microbiomes perform many vital physiological functions that benefit their host organism, comprising digestion, producing essential amino acids and vitamins, regulating the immune system, providing resistance to disease, and even modifying appetite and behavior. Yet we know very little about the functions of hundreds or thousands of microbial species and their associated primary and secondary metabolites in mammalian GI tracts. The variety of microbes in a single individual at different points of the GI tract is staggering. Due to the complexity of this microbial ecology in a single individual and the variability among individuals, there exists a need to routinely sample and analyze the microbial community living in all regions of the GI tract, along with their associated metabolites, as well as their interactions with the host. Microbial secondary metabolites play a key role in the two way communication between the microbes and their hosts and can greatly impact the physiological state of the host. The analyses of the gut microbes can correlate to states of health and disease, as well as guide and measure the effect of treatment.

SUMMARY OF THE DISCLOSURE

The present invention relates to devices for collecting gastrointestinal samples using a capsule-shaped device that is swallowed, a targeting mechanism, and a sealing mechanism for the device to prevent sample contamination after the sampling event.

In an initial aspect, a device for collecting gastrointestinal samples is provided. The device comprises a tube-shaped hollow body comprising an open end and a closed end. A portion of the tube shape-device hollow body comprises a sample collecting member. The open end of the tube shaped hollow body comprises a sampling opening. The device further comprises one or more covering elements that dissolve, erode, degrade, rupture, or dislocate in the gastrointestinal tract to target the location of sampling at the appropriate location in the GI tract. The device further comprises a filtering element to control the size of particles sampled by the device, and a sealing element to preserve the integrity and prevent contamination of the collected sample.

In an additional aspect, the device is surrounded by a capsular shell, sleeve or collar that comprise one or more covering elements that dissolve, solubilize, erode, degrade, soften, weaken or rupture in the gastrointestinal tract.

In another aspect, the device initiates sampling in a gastrointestinal region of interest of a subject. The initiation of the sampling is determined by the degradation, erosion, dissolution, weakening, softening, rupturing or dislocation of the one or more covering elements in conjunction with the unfolding and/or expansion force of the elastically compressed device hollow body and/or a pressure differential across the sampling opening created by the unfolding and/or expansion of the elastically collapsed device hollow body.

In another aspect, the differential under pressure or vacuum generated by the hollow body is in the range of 0.5 to 4 pounds per square inch as measured across the sampling openings when the hollow body is in the fully collapsed state.

In another aspect, the sealing element seals with a pressure of at least 0.5 pounds per square inch to create a seal capable of preventing contaminating bacteria from entering into the device.

In an additional aspect, at least one of the covering elements is water-insoluble and ruptures based on the swelling of an underlying layer after a set time delay or when exposed to the GI luminal contents at a certain pH range.

In another aspect, device comprises a thin-shell device hollow body, a filtering element, a sampling opening, a compression spring actuator, and a fully soluble covering element that maintains the actuator in a compressed state.

In a further aspect, the device is provided in packaging that limits any strain or any change of dimension of the outer envelope of the device until the device is removed from the packaging.

In a further aspect, the device for collecting gastrointestinal samples comprises a hollow body, a sampling opening, and at least one covering element.

In a further aspect, at least one covering element is configured for maintaining the hollow body in a compressed configuration.

In a further aspect, at least one covering element covers a soluble capsule shell that is configured for maintaining the hollow body in a compressed configuration.

In a further aspect, at least one covering element is configured for maintaining the hollow body in a kinked configuration.

In a further aspect, at least one covering element is configured to block the flow of gastrointestinal samples into the hollow body.

In a further aspect, the device comprises a first covering element and a second covering element, wherein the first covering element surrounds the second covering element.

In a further aspect, the device comprises a first covering element and a second covering element, wherein the first covering element prevents fluids from contacting the second covering element.

In a further aspect, the device comprises a first covering element that includes a material that degrades at a pH of 5 or higher, and a second covering element that includes material that degrades at a rate that is independent of pH in the range of pH 5 to 8.

In a further aspect, the device comprises a sampling opening that is not covered by the second covering element.

In a further aspect, the device comprises a first covering element, a second covering element, and a third covering element, wherein the first covering element covers the second covering element and the second covering element covers the third covering element.

In a further aspect, the first covering element includes a material that degrades at a pH of 5 or higher, the second covering element includes material that degrades at a rate that is independent of pH in the range of pH 5 to 8, and the third covering element includes a material that degrades at a pH of 6 or higher.

In a further aspect, the hollow body is folded up onto itself and creased along the long axis to within a covering element or capsule shell.

In a further aspect, the hollow body is creased along the long axis and folded axially within a covering element or capsule shell.

In a further aspect, the hollow body is twisted axially and folded up onto itself along the long axis within a covering element or capsule shell.

In a further aspect, at least one covering element is fully soluble in a gastrointestinal tract within 12 hours.

In a further aspect, the device comprises covering elements and capsule shells that are all fully soluble in a gastrointestinal tract within 12 hours.

In a further aspect, at least one covering element includes material that degrades in a pH dependent manner.

In a further aspect, at least one covering element includes material that degrades at a rate that is independent of pH in the range of pH 5 to 8.

In a further aspect, the hollow body is a radially collapsed tube within said at least one covering element.

In a further aspect, at least one covering element is configured for degrading primarily along one axis to thereby allowing the hollow body collapsed therein to gradually return to an un-collapsed state.

In a further aspect, at least one covering element swells and separates from the hollow body when exposed for sufficient time to the fluids of the gastrointestinal tract.

In a further aspect, at least one covering element swells and separates from the hollow body when exposed to the fluids of a specific pH in the range of pH 5 to 8.

In a further aspect, the device for collecting gastrointestinal samples comprises a hollow body with a plurality of covering elements covering discrete locations along the hollow body.

In a further aspect, the plurality of covering elements cover the hollow body via a kinking mechanism.

In a further aspect, the plurality of covering elements degrade at different times or different pH levels in a gastrointestinal tract.

In a further aspect, the device for collecting gastrointestinal samples comprises a plurality of interlinked hollow bodies, each of the hollow bodies includes a sampling opening, and each includes a covering element that degrades at a set time interval or set pH range in the gastrointestinal tract.

In a further aspect, the device for collecting gastrointestinal samples comprises a hollow body having a sampling opening and a filtering element positioned in fluid communication with the sampling opening.

In a further aspect, the filtering element includes an open cell foam.

In a further aspect, the filtering element includes an open cell foam that is hydrophobic.

In a further aspect, the filtering element includes a woven or non-woven mesh.

In a further aspect, the filtering element includes a woven or non-woven mesh that is hydrophobic.

In a further aspect, the filtering element includes fibers.

In a further aspect, the filtering element includes fibers that are hydrophobic.

In a further aspect, the filtering element includes pores for allowing particles smaller than 50 microns through the filtering element.

In a further aspect, the filtering element is positioned adjacent to a covering element.

In a further aspect, the filtering element is covered or impregnated by a covering element covering the sampling opening of the hollow body.

In a further aspect, the filtering element includes a sleeve of porous material positioned around at least a portion of the hollow body and the sampling opening.

In a further aspect, the device for sampling gastrointestinal samples comprises a hollow body containing a solid, dehydrated or highly concentrated preservation agent.

In a further aspect, the preservation agent inhibits RNAse and/or DNAse activity.

In a further aspect, the preservation agent comprises a salt.

In a further aspect, a method of speeding up the rate of passage of a device through a small intestine comprises ingesting a first meal of between 50 to 250 kilocalories, swallowing the device, waiting for the device to transition into the duodenum and the stomach to empty, and eating a second meal of between 25 to 100 kilocalories to trigger an additional cycle of a phase III migrating motor complex within 2 hours following the second meal, thereby speeding up a rate of passage of the device through the small intestines.

In a further aspect, at least one of the first or the second meals is blended in order to reduce gastric emptying time.

In a further aspect, the step of eating a second meal of between 25 to 100 kilocalories to trigger an additional cycle of a phase III migrating motor complex is repeated at least once following a delay of 1 to 2 hours.

In a further aspect, a method of slowing down the rate of passage of a device through a small intestine comprises ingesting a first meal of between 50 to 500 kilocalories, swallowing the device, waiting for the device to transition to the duodenum, and eating a second meal of between 100 to 700 kilocalories to delay onset of a phase III migrating motor complex for at least 2 hours following the second meal, thereby slowing down a rate of passage of the device through the small intestines.

In a further aspect, the user is instructed to wait at least 1 hour after eating a first meal for the stomach to become acidic before swallowing the device.

In a further aspect, the time between ingestion of the first meal and swallowing the device is based on a time range calculated by dividing the number of kilocalories of food eaten by the ratios of 1 kilocalorie per minute and 5 kilo calories per minute, or preferably by the ratios of 2 kilocalorie per minute and 4 kilo calories per minute.

In a further aspect, the time between swallowing the device and ingestion of the second meal is 1 to 2 hours.

In a further aspect, the time for swallowing the device and/or eating the second meal is based on detection of the phase III migrating motor complex in a gastrointestinal tract.

In a further aspect, the detection of the phase III migrating motor complex in a gastrointestinal tract is conducted using audible sensing means.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9*a-c* illustrate a cross sectional view of the assembly of a device comprising two covering elements.

DETAILED DESCRIPTION OF THE INVENTION

Figure 1:
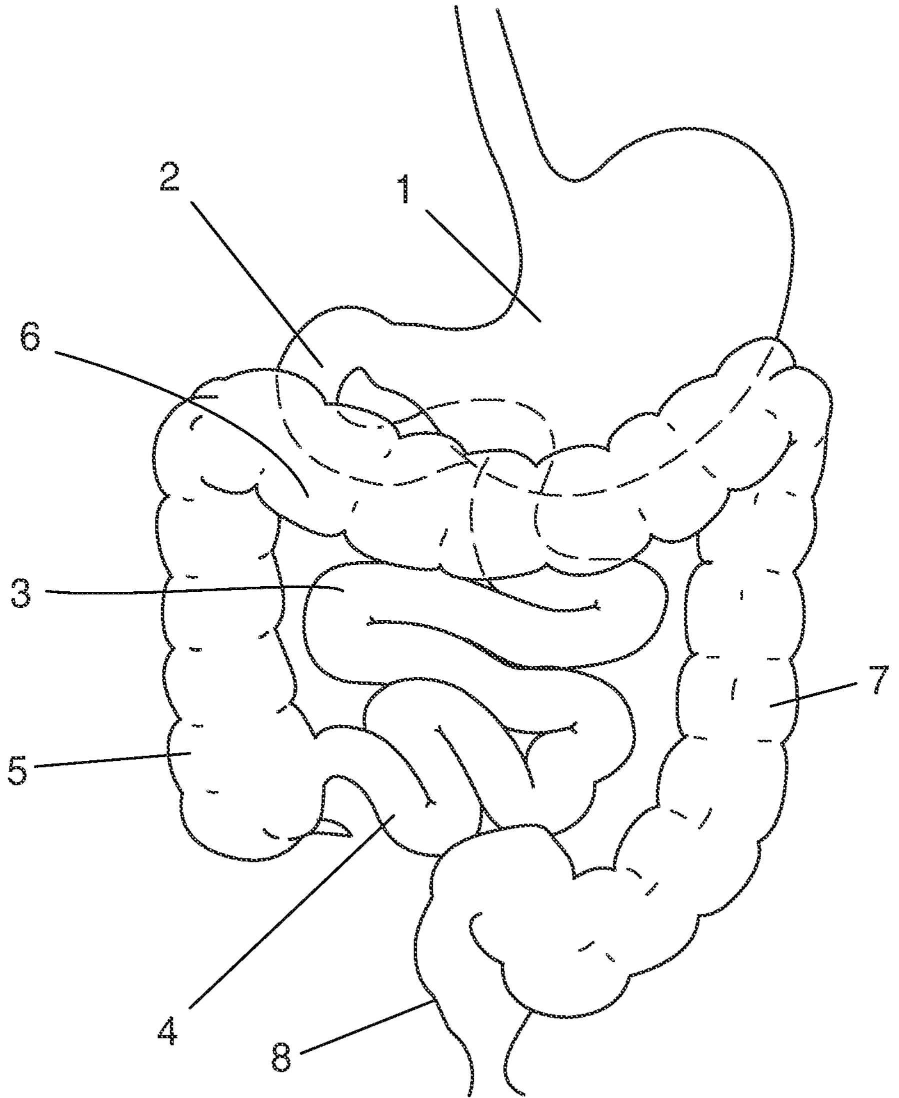
FIG. 1 illustrates the anatomy of the human gastrointestinal tract.

As used herein, the term "gastrointestinal samples" comprises liquids, digestive juices, mucus, microbes, metabolites, cells, cell fragments, carbohydrates, fats, lipids, proteins, peptides, immune system molecules, immune system cells, blood, hemoglobin, food particles, acids, bases, gases, small molecules, hormones, nucleic acids, drugs, pro-drugs, drug metabolites, volatile molecules, dissolved or free gases, and other molecules present in the GI tract from the mouth to the anus. As used herein, the term "microbe" comprises one or more species or strains of microscopic agents from the three domains eubacteria, eukarya and archaea as well as viruses such as phages. As used herein, a group of microbes, or a microbial population, taken as a whole is referred to as a "microbiota" and when the group is quantitated or measured in some manner it is referred to as a "microbiome." As used herein, the terms "immune system molecules or immune system cells" comprise all forms of lymphocytes, leukocytes, antigen-presenting cells, antibodies, antigens, markers of inflammation, c-reactive protein (CRP), antimicrobial molecules, proteases, cell signaling proteins, cytokines, chemokines, hormones, neurotransmitters, interleukins, vitamins, major histocompatibility (MHC) molecules, complement system molecules, anti-viral molecules, and the like.

As used herein, the term "active agent" comprises drugs, pro-drugs, nutritional supplements, prebiotics, probiotics, postbiotics, synbiotics, microbes, immune system molecules, immune system cells, immune system modifiers, dyes, combinations of the above, and the like.

As used herein, the term "degrade" means to dissolve, erode, rupture, burst, hydrolyze, hydrate, redisperse, soften, gel, swell, become lubricious, becomes permeable to water, lose strength, or lose friction.

As used herein, the term "degradable material" comprises "moisture degradable material" and also "enteric degradable material" as described more fully below.

As used herein, the term "moisture degradable material" comprises materials that degrade when exposed to moisture at a broad range of pH levels, or in a narrow range of pH levels, at a broad range of times or in a narrow range of times, and in the presence or absence of human or microbial enzymes that can metabolize or degrade such a material. Examples of moisture degradable materials comprise polyvinyl alcohol (PVA), polyvinyl acetate, polyvinyl acetate phthalate (PVAP), polyallylamine hydrochloride, polyvinyl chloride, polyvinylpyridine acrylic acid, fatty acids, waxes, shellac, plant fibers, paper, hydroxypropyl cellulose (HPC), hydroxyethyl methyl cellulose (HEMC), carboxymethyl cellulose (CMC), hydroxypropyl methylcellulose (HPMC), cellulosic derivatives, starch, ethyl cellulose, cellulose acetate phthalate (CAP), cellulose acetate succinate, hydroxypropyl methyl cellulose phthalate, hydroxypropyl methyl cellulose acetate succinate, paper, cardboard, methyl methacrylate, methacrylic acid, methyl acrylate-methacrylic acid copolymers, polyacryl, cellulose acetate, trimellitate, sodium alginate, zein, starch, pectin, gelatin, agar, agarose, cross-linked gelatin, carbohydrates, gum arabic, salts, sodium hypochlorite, lithium hypochlorite, calcium hypochlorite, dichlor, trichlor, sugars, polyols, proteins, hydrogels, as well as polymers, copolymers, acetates, sheets, coatings, foams, mixtures, or derivatives thereof. The functionalities of the moisture degradable material comprise protecting the device from exposure to gastrointestinal content until the desired location in the GI tract is reached, allowing the starting and/or stopping of the sampling of gastrointestinal fluids, and/or acting as a sanitizing bactericide to stop all metabolic processes when dissolved in the collected samples. By way of example, solid salt such as sodium chloride that is in fluid communication with the collecting member will dissolve when gastrointestinal fluids are introduced into the sampling capsule. The solid salt acts to resist the motion of an actuator. When dissolved, the salt can no longer physically prevent the sealing of the sampling capsule by the actuator. Furthermore, the resulting high dissolved salt concentrations in the collecting member kills the microbes in the device, thereby helping preserve the biomolecules therein for analysis at a later time.

As used herein, the term "enteric degradable material" comprises compounds and coating techniques that enable the collecting member of a device to only come into fluid communication with a portion of the GI tract that is distal to the stomach, specifically at pH level of 5 or higher. Sample enteric degradable materials comprise methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, and combinations or derivatives thereof. The enteric degradable materials disclosed herein control the flow of fluid into a device at a point distal to the stomach.

Enteric degradable materials can be combined with pH-independent degradable materials that degrade or erode mainly after the device has had sufficient time to traverse at least a portion of the small intestines and/or enter into the colon. By way of example, a device is coated with a pH-independent material such as a cellulose-based material and then further coated with an enteric degradable material such as methacrylic acid that only dissolves at a pH level of 5 or higher that is present in the small intestine. The external enteric degradable material protects the device during the transit through an acidic stomach. The enteric degradable material degrades in the pH of the small intestine, thereby exposing the next coating of cellulose, which is a pH-independent material. The cellulose coating takes 4 hours to degrade which protects the device through the remaining 3 hour transit through the small intestines. Finally, when the cellulose coating degrades in the colon, the device collects a gastrointestinal sample in the colon. As used herein, the term "colonic targeting" refers to compounds and coating techniques that enable the collecting member of a device to only come into fluid communication with a portion of the GI tract that is distal to the small intestine. Colonic targeting materials comprise materials that are preferentially degraded at pH levels, gas content, color, lumen size, enzymes, metabolism or microbes that are preferentially present in the colon relative to the small intestines. Example materials that are useful coatings for colonic targeting comprise methacrylic acid, methyl methacrylate-methacrylic acid copolymers, cellulose-based materials, starch, pectin, chitosan, guar gum, dextran, and combinations or derivatives thereof. Furthermore, colonic targeting can be achieved by speeding up the rate of passage of the sampling device through the small intestine using methods described herein.

Enteric drug delivery technologies are used to control the delivery of active agents out of a capsule, pill or tablet into the hollow body at a point distal to the stomach. For example, flow of an active agent out of a capsule, pill or tablet can be achieved via slow diffusion of the molecular-sized active agent through a swollen and hydrated enteric coating. The goal of most enteric delivery systems is to release an active agent at a rate that is independent of the concentration of the active agent in the tablets. So called zero-order release kinetics describe systems where the active agent release rate is constant over a period of time.

In contrast, flow of gastrointestinal samples into a sampling device requires complete prevention of flow into the device until the desired location in the GI tract is reached, followed by rapid bulk flow of liquid with micron-sized objects such as microbes and food particles into the device through a fully dissolved, ruptured, removed or eroded covering element in a time period of 20 minutes or less to ensure high resolution sampling of a specific GI region. If sampling were to occur gradually via a diffusion-like mechanism for more than 20 minutes, the device could transition to a different region of the GI tract and upstream or downstream microbes and analytes could contaminate the samples collected at the desired GI region. Based on experiments done by the inventor, normal peristalsis carries the sampling device through a 600 centimeter long small intestine in approximately 180 minutes, or an average velocity of 200 cm per hour. Therefore, a maximum sampling duration of 20 minutes would provide an average resolution of sampling location of 70 cm or less. Assuming that the exact sample initiation time of the device in the 600 cm long small intestines is somewhat random, a sampling resolution of 70 cm, or 20 minutes, will reduce the chance of sampling across a sharp regional boundary such as stomach/small intestine transition or a small intestine/colon transition to about 12%. A sampling duration of more than 20 minutes increases the likelihood of sampling across a major regional transition which is highly undesirable given the large changes in microbiota present at the different regions of the GI tract. Therefore, enteric coatings that work for drug delivery by swelling or increasing porosity in order to release active agents through submicron pores over a time period of greater than 20 minutes will not work well for controlling the function of a sample collection device that has to collect up to one milliliter of fluids with partially digested food particles of up to 50 microns in diameter into the collecting member within 20 minutes after the start of sampling at the desired sampling location.

As used herein, the term "swelling material" comprises materials that when exposed to fluids expands in at least one direction. Example swelling materials comprise hydrogels, hydrocolloids, super absorbing polymers, sodium polyacrlyate, polyacrylamide copolymer, croscarmellose sodium, cross-linked polyvinyl pyrollidone, ethylene maleic anhydride copolymer, carboxymethylcellulose, hydroxypropyl cellulose, polyvinyl alcohol copolymers, cross-linked polyethylene oxide, hydrophilic polyurethane, hydroyethylmethacrylate (HEMA), starch grafted copolymer of polyacrylonitrile, sodium starch glycolate, crospovidone, open cell foams, cellulose, gelatin, pectin, chitosan, dextran, alginate, paper, cardboard, gelatin, agar, agarose, collagen, glycosaminoglycan and the like.

As used herein, the term "pH independent material" comprises any moisture degradable material with a degradation rate that is not affected by more than 50% in the pH range of 5 to 8 typically found in the GI tract from the small intestine to the colon. Examples of such materials comprise polyvinyl alcohol, polyvinyl acetate, fatty acids, waxes, shellac, plant fibers, paper, hydroxypropyl cellulose (HPC), hydroxyethyl methyl cellulose (HEMC), carboxymethyl cellulose (CMC), hydroxypropyl methylcellulose (HPMC), cellulosic derivatives, starch, ethyl cellulose, carrageenan, gellan, meth-/acrylate copolymers with trimethyl-ammonioethylmethacrylateas a functional group, neutral polymer of meth-/acrylates, sugars, polyols, isomalts, crystals of salts, combinations of the above, and the like.

As used herein, the term "pH dependent material" comprises any moisture degradable material with a degradation rate that is increased or decreased by more than 50% at the extreme end of the pH range from 1 to 8 typically found in the GI tract from the stomach to the colon. Examples of such materials comprise anionic polymers with methacrylic acid as a functional group, cationic polymer with dimethylaminoethyl methacrylate as a functional group, hypromellose acetate succinate and the like.

As used herein, the term "rupturable material" comprises materials that fracture when experiencing strain of up to 50%. In another aspect, rupturable materials comprise relatively rigid polymers, so that the area under the stress-strain curve of a film made from the rupturable material is between 0.005 to 0.4 mega Pascal. Examples of rupturable materials comprise ethyl cellulose, cellulose acetate, cellulose acetate propionate and the like. Such materials may comprise plasticizers, pore forming materials, hydrophilic materials to increase water permeability, and/or particles that swell when exposed to moisture to physically weaken the rupturable material.

As used herein, the term "filtering element" comprises meshes, open cell foams, porous materials, loose fibers, compressed fibers, crosslinked fibers, spun fibers, tangled fibers, pores formed in membranes, screens, woven and non-woven meshes, and the like. At least a portion of the surface of the filtering element can be hydrophobic with contact angle of water greater than 90 degrees, super-hydrophobic with contact angle of water greater than 150 degrees, or hydrophilic with contact angle of water less than 90 degrees.

Unless otherwise defined, all technical and scientific terms used herein have the same meaning as commonly understood by one of ordinary skill in the art to which this invention belongs. Although methods and materials similar or equivalent to those disclosed herein can be used in the practice of the present invention, suitable methods and materials are disclosed below. In case of conflict, the patent specification, including definitions, will control. In addition, the materials, methods, and examples are illustrative only and not intended to be limiting.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

FIG. 1 shows the regions of the human gastrointestinal (GI) tract that are sampled by the device and methods described herein. Food enters stomach 1 where muscles mix the food and liquid with digestive juices. The stomach slowly empties its contents, called chyme, into the duodenum 2, also referred to as the proximal portion of the small intestine. The sharpest and most reliable transition of pH in the GI tract occurs between the stomach, with a pH range of 1 to 3.5, and the duodenum, with a pH range of 5 to 6, but sometimes spiking down to pH 3 and up to pH 8. This sharp pH transition makes this region relatively easy to target with enteric degradable materials. The muscles of the small intestine mix food with digestive juices from the pancreas and liver, and push the mixture forward into the jejunum 3, also referred to the as mid portion of the small intestine, for further digestion. The walls of the small intestine absorb the digested nutrients into the bloodstream until ileum 4, also referred to as the distal portion of the small intestine, is reached. As peristalsis continues, the undigested components of the food move into the ascending colon 5, also referred to as the right colon or proximal colon portion of the large intestine where complex carbohydrates are fermented by microbes. Waste products from the digestive process, include undigested parts of food, fluid, and older cells from the lining of the GI tract, get transferred into the transverse colon 6, also referred to as the mid colon. The descending colon 7, also referred as the left colon or distal colon portion of the large intestine absorbs water and changes the waste from liquid form into solid stool. Peristalsis helps move the stool into rectum 8 and from there into the toilet during a bowel movement. The pH levels and transit time in the various regions of the GI tract are described more fully in table 1 below.

TABLE 1 pH and transit time of the human GI tract.
Ref: Gut, 1988, 29, 1035-1041.

| GI region | Mean pH (range) | Standard deviation | Time spent in each region |
|---|---|---|---|
| Stomach | (1.0-3.5) | n/a | Up to 3 hours |
| Duodenum | (5.0-6.0) | n/a | Up to 1 hour |
| Jejunum | 6.6 | 0.5 | Up to 1 hour |
| Ileum | 7.5 | 0.5 | Up to 1 hour |
| Right colon | 6.4 | 0.6 | Up to 6 hours |
| Mid colon | 6.6 | 0.8 | Up to 8 hours |
| Left colon | 7.0 | 0.7 | Up to 12 hours |

The gastrointestinal device disclosed in this patent application is intended to sample discrete regions of the GI tract and then seal to prevent contamination of the collected sample by downstream GI contents. In the case of sampling the microbiota of the GI tract, the sealing function after sample collection plays a crucial role in maintaining sample integrity. Bacteria are around 2 microns in size along their narrow dimension. Forming a bacteria-tight seal which does not let through anything greater than 0.22 microns in diameter is therefore crucial for proper function of the gastrointestinal collection device. Given the increasing bacterial densities further down the GI tract, it is vital to be able to tightly seal the capsule after sampling. If the seal is not capable of blocking the passage of bacteria, upstream regions will inadvertently appear to be populated by bacteria that are really present in the downstream regions of the GI tract. It has been recently discovered that the bacterial loads increase exponentially in the different regions of the GI tract as shown in Table 2 below. Prior art sampling devices were focused on analyzing the chemistry of the fluids of the GI tract where the effect of a minor contaminant is negligible. A single nanoliter (10^−9 liter) of colonic contents making its way into a milliliter (10^−3 liter) of small intestine sample would have negligible impact on the chemical makeup of the fluid due to the million fold dilution of the contaminant. Therefore, prior art devices were not designed in a manner that prevents any form of bacterial contamination after sample acquisition in a sampling duration of 20 minutes or less. The present invention, in contrast, is intended to collect the microbiota in each region of the GI tract without any downstream contamination. From Table 2, it is disclosed that just a single nanoliter (10^−9 liter) of colonic contents contaminating a 0.33 milliliter (3.3×10^−4 liter) capacity capsule intended to sample the duodenum would introduce around 100,000 colonic bacteria into the sample, which is approximately 30 times more than the 3,000 or so duodenal bacteria present in the capsule, falsely making it appear that colonic bacteria are present in the duodenum of the subject. Therefore, it is advantageous to seal the collecting member with a sealing force of at least 0.5 pounds per square inch to avoid opening of the seal during the jostling of the device in the GI tract and in subsequent handling. Furthermore, the collecting member needs to be sealed such that objects 0.22 microns or larger such as bacteria cannot pass the sealing element after the sample collection process is complete. At the same time, the sealing element needs to allow a sufficient volume of the desired sample to flow into the collecting member of the device at the intended sampling site.

TABLE 2

Approximate bacterial densities as a function of GI location

| GI region | Approximate number of colony forming units per milliliter of sample collected |
|---|---|
| Stomach | 100 |
| Duodenum | 1,000 |
| Jejunum | 10,000 |
| Ileum | 10,000,000 |
| Cecum | 10,000,000,000 |
| Colon | 100,000,000,000 |

One way valves that are neutral such as duckbill valves, or actively biased such as umbrella valves, can constitute the sealing element of the sampling opening 42. However, there are particles of undigested food up to 1 mm in size in the GI tract that can get caught in the one way valve mechanism and foul the valve's seal. One way valves, by their nature, open up with only a minimal crack to let fluid by in the free-flow direction as a result of a pressure differential across the valve. The particles present in the gastrointestinal samples will get trapped and accumulate in the crack of the one way valve mechanism. Therefore, a residual gap is likely in a one way valve mechanism, which leaves sufficient room for downstream bacteria to contaminate the collected gastrointestinal samples as described above.

In a further embodiment, oil or grease is used between the sealing element and itself, such as in the case of a duckbill valve, or the sealing element and the sealing seat, such as in the case of an umbrella valve, in order to improve the sealing ability of the valve.

Figure 11A:
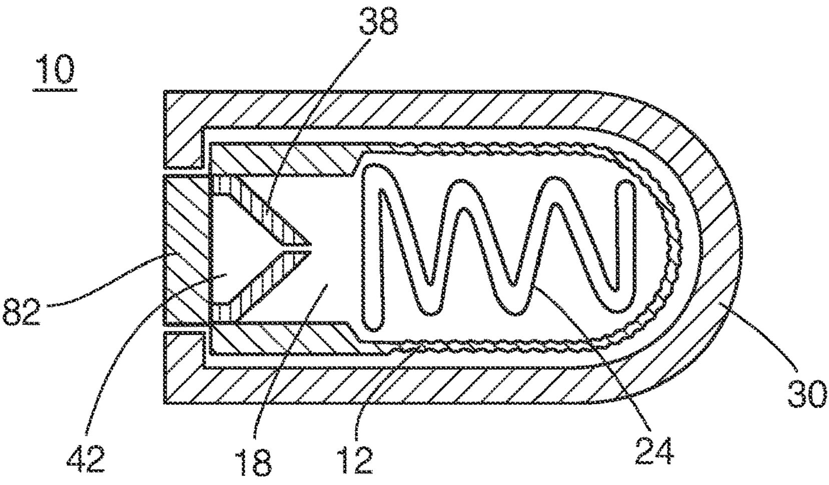
FIGS. 11*a-b* illustrate a cross sectional view of the device comprising an axial expansion mechanism constrained by a clamp-shaped covering element.
Figure 11B:
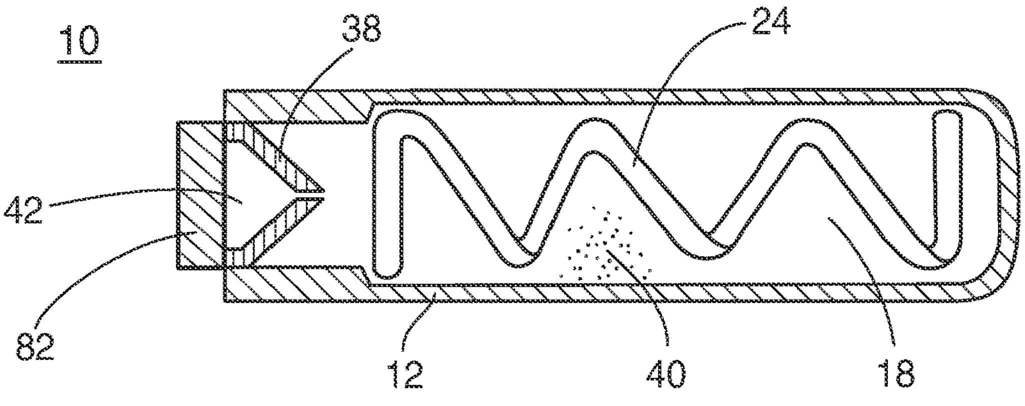

In a further embodiment, as illustrated in FIGS. 11*a-b*, device 10 comprises a thin-shell hollow body 12, filtering element 82, sampling opening 42, a compression spring actuator 24 and fully degradable covering element 30 that maintains actuator 24 in a compressed state. Actuator 24 is a compression spring that pushes hollow body 12 in an axial direction to initiate sampling of gastrointestinal samples. Hollow body 12 comprises a single piece of flexible polymer less than 0.3 mm thick, preferably less than 0.2 mm thick, with no sliding seals and with insufficient elastic recovery force when returning to its relaxed position to force samples into collecting member 18 via sampling opening 42 and/or sealing element 38. Rather, actuator 24 supplies the required axial force to pull the samples into collecting member 18 and to expand collapsed hollow body 12. As show in in FIG. 11*a*, when packaged for swallowing before sample collection, actuator 24 is compressed in a high energy state by covering element 30 and hollow body 12 is collapsed, crumpled, or invaginated around actuator 24. Covering element 30 is on the outside of hollow body 12 and does not cover sampling opening 42 or filtering element 82. By leaving sampling opening 42 and filtering element 82 exposed, a partially degraded covering element 30 does not interfere with the flow of gastrointestinal samples into collecting member 18. Covering element 30 resists the axial force of actuator 24. Covering 30 comprises either a pH dependent or a pH independent moisture degradable material, depending on the GI region being targeted. As illustrated in FIG. 11*b*, after the appropriate pH range in the GI tract is reached, or the appropriate time in the GI tract has elapsed, covering element 30 degrades and can no longer mechanically restrain the axial force of actuator 24. Covering element 30 is made from a material that fully degrades or solubilizes in the gastrointestinal tract within 12 hours so as to not create a blockage of the lumen of the small intestines by a foreign object that is bigger in diameter and less flexible than hollow body 12. Preferably, the restraining aspect of covering element 30 occurs in a binary, that is "all or nothing" manner. Covering element 30 fully restrains actuator 24. Then, within a 20 minute window, preferably within a 10 minute window or even more preferably within a 5 minute window of the initiation of sampling, covering element 30 degrades and no longer restrains actuator 24 thereby ensuring sampling in a narrow geographical window of 70 cm or less Upon the degradation of covering element 30, actuator 24 expands axially towards the relaxed state, thereby initiating the collection of gastrointestinal samples. Actuator 24 is inside collecting member 18. Hollow body 12 is a highly flexible and impermeable barrier, envelope, membrane, thin shell, or bag that contains gastrointestinal samples, but is incapable of generating the minimum 0.5 pounds per square inch of pressure required to pull the gastrointestinal samples into collecting member 18. The expansion of actuator 24 within collecting member 18, however, does provide at least the 0.5 pounds per square inch of pressure required to pull the samples through sealing element 38 and into collecting member 18. Importantly, device 10 comprises no sliding seals, but rather relies on a closed outer membrane to contain the collected gastrointestinal samples. The diameter and shape of collecting member 18 is determined by the diameter of the compression spring actuator 24. Actuator 24 and hollow body 12 are not connected to one another along their entire length in order to allow for relative motion between the two. Furthermore, both actuator 24 and device hollow body 12 are non-rigid, and despite being 2 cm in length or longer, can elastically bend along a radius of curvature of 2 cm or less, which allows for easy transit through the tortuous small intestine anatomy. Additionally, hollow body 12, which is made of a polymer that could experience creep or plastic deformation during long term storage, does not need to store the elastic energy required for expansion. Rather, actuator 24 which is a spring made of metal, retains full energy of expansion over time.

Figure 12A:
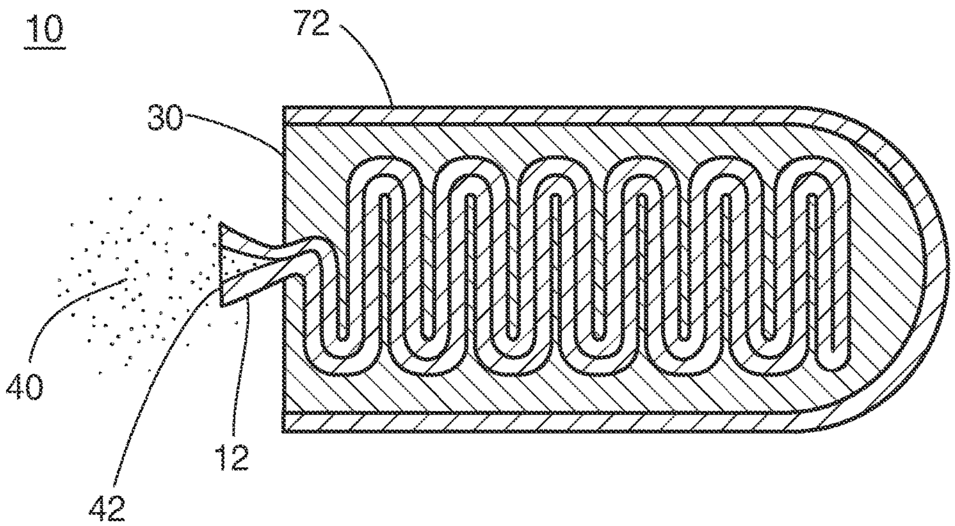
FIGS. 12*a-b* illustrate a cross sectional view of the device comprising a collapsed tube-shaped hollow body embedded in a covering element within an open-faced non-soluble capsule shell.
Figure 12B:
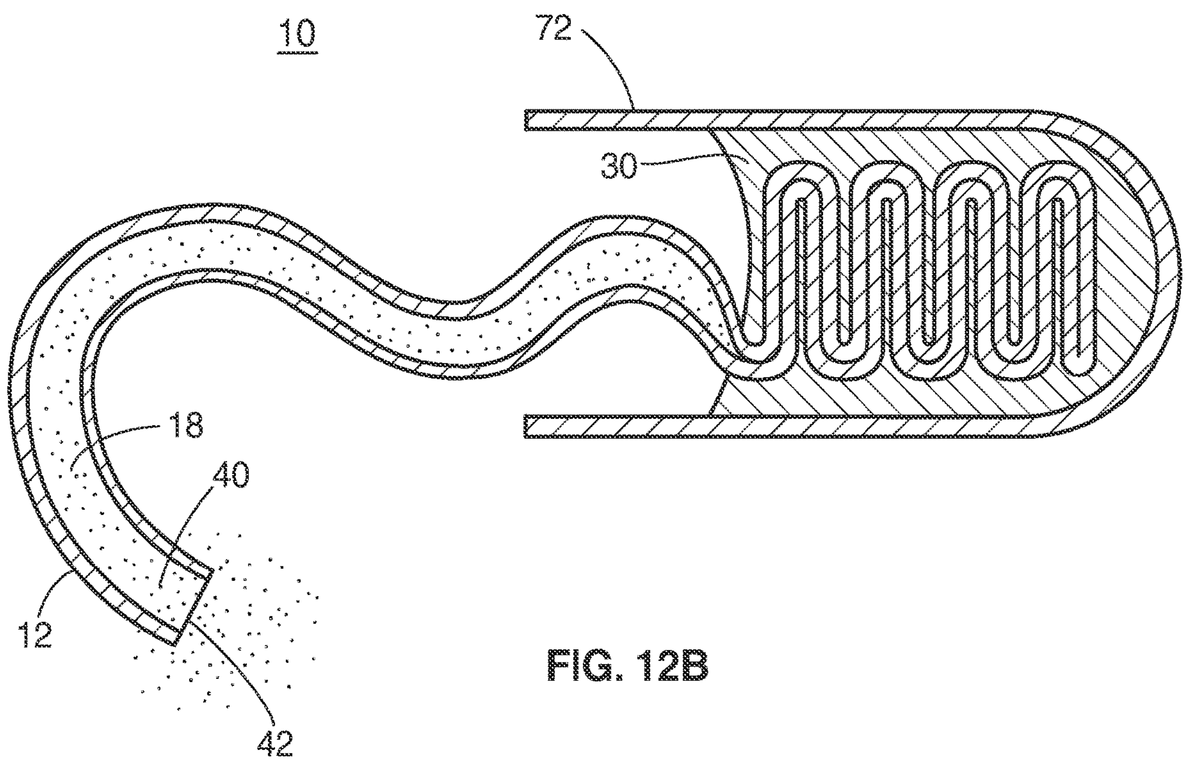

In a further embodiment, as illustrated in FIGS. 12*a-b*, device 10 comprises hollow body 12 configured as a long tube with a closed distal end and an open proximal end that forms sampling opening 42. Hollow tube 12 is elastic and is radially collapsed and embedded in the collapsed configuration inside covering element 30. Covering element 30 and hollow body 12 are contained within insoluble capsule shell 72 that enables a limited area of contact between covering element 30 and the fluids of the gastrointestinal tract. During the passage of device 10 through the gastrointestinal tract, covering element 30 degrades in a pH-dependent or pH-independent manner primarily along one axis, which thereby allow hollow body 12 to gradually return to an un-collapsed state. In the process of expansion to an un-collapsed state, hollow body 12 pulls in gastrointestinal samples 40 through sampling opening 42. Gastrointestinal samples 40 form a linear array inside hollow body 12. This embodiment enables continuous sampling, so that large regions of the GI tract can be sampled in their entirety by swallowing a single device 10.

In a further embodiment, device 10 is provided in packaging that resists any strain due to actuator 24 or any elastic deformation forces in device hollow body 12 from acting over time to deform covering element 30. An example of such packaging comprises a hard plastic package that limits any change of dimension of the outer envelope of device 10 comprising a high energy state actuator 24 or elastic deformation of device hollow body 12. The packaging resists any strain or creep towards a lower energy state until device 10 is removed from the packaging. In this manner, in the embodiments wherein covering element 30 acts as a mechanical restraint to prevent sampling until covering element 30 degrades, then covering element 30 is not under any stress by actuator 24 or an elastic deformation of hollow body 12 until device 10 is removed from the packaging.

A significant challenge to collecting gastrointestinal samples as experimentally discovered by the present inventor is that gastrointestinal digesta comprises mucus and colloids that form a cohesive sludge in the GI tract that is hard to collect into device 10. Passage of the mucus and colloids through sample opening 42, particularly through a narrow passageway less than 2 mm in diameter or at high velocities, tends to lead to aggregation and flocculation of the colloid particles such as bacteria, undigested food particles, high-molecular-weight macropolymers in mucus, and relatively small molecular components of organic matter auto-assembled in supramolecular associations in the process of becoming solid stool and form a sludge of mud-like consistency. As a result, a solid plug is formed by these substances in sampling opening 42 preventing the complete filling of collecting member 18. Alternatively, a filter cake of the aggregated particles is formed on filtering element 82. The filter cake grows in the course of collecting gastrointestinal samples, becoming thicker as particulate matter is retained. With increasing layer thickness, the flow resistance of the filter cake increases. After a time, and before the complete filling of collecting member 18, the filter cake fouls filtering member 82 and stops all further flow of fluids into collecting member 18.

In a further embodiment, an aggregated plug comprising digesta is allowed to form in sampling opening 42 or on filtering element 82 and serves to seal collecting member 18 and prevents any further gastrointestinal samples from entering into collecting member 18.

In a further embodiment, the luminal surfaces of sampling opening 42 and/or of sealing element 38 are hydrophobic or super-hydrophobic in order to prevent adherence and aggregation of digesta particles flowing through sampling opening 42 and/or of sealing element 38 into collecting member 18.

Figure 5A:
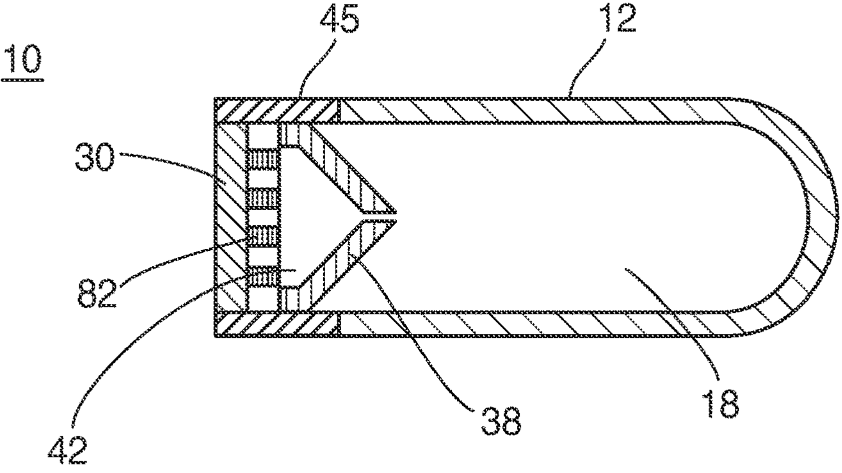
FIGS. 5*a-c* illustrate a cross sectional view of three embodiments of the device comprising a filtering element.
Figure 5B:
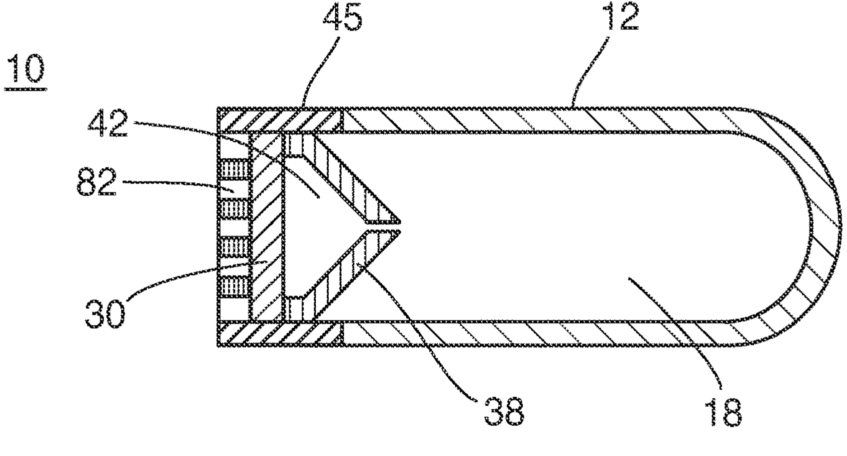
Figure 5C:
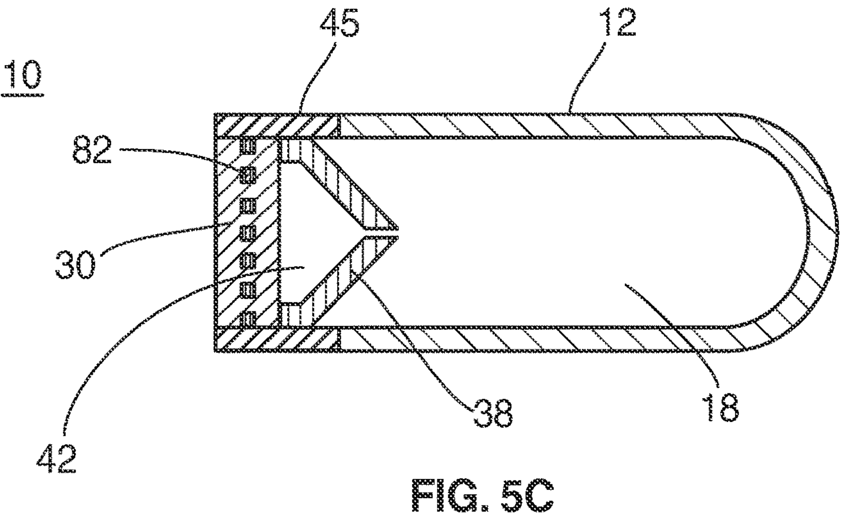

In one embodiment, and with reference to FIG. 5*a-c*, device 10 comprises filtering element 82 which prevents the fouling of sampling opening 42 and/or sealing element 38. Device 10 also comprises covering element 30 which is configured as a membrane to block the flow of gastrointestinal samples into the collecting member 18 of hollow body 12. Covering element 30 is positioned adjacent to filtering element 82. In the embodiment illustrated in FIG. 5*a*, covering element 30 is seated external to filtering element 82, which is seated external to one-way valve sealing element 38, which in turn separates collecting member 18 from the outside environment. This configuration is advantageous in that covering element 30 is supported by filtering element 82 and covering element 30 which comprises a degradable material slowly degrades until the pores of filtering element 82 allow passage of gastrointestinal samples into collecting member 18 while preventing particles greater than the pore size to pass through filtering element 82. This embodiment therefore prevents fouling of sealing element 38, shown here as a duck bill valve mounted in housing 45. The order of elements of device 10 in this embodiment, from the direction of gastrointestinal tract towards collecting member 18, is covering element 30, filtering element 82, sealing element 38 and collecting member 18.

In a further embodiment illustrated in FIG. 5*a*, filtering element 82 physically supports covering element 30 which is in the form of a thin membrane shape comprising a degradable material. In this manner, filtering element 82 prevents a sudden inward rupture of the thin membrane-shaped covering element 30 due to the under-pressure inside collecting member 18. The degradation time or dissolution of covering element 30 is more predictable when physically supported, as opposed to a degradation mechanism whereby the membrane ruptures suddenly due to a loss of mechanical strength across the full span of covering element 30.

In a further embodiment, capsule shell 72 is coated by covering element 30. In this embodiment, filtering element 82 is still mounted in housing 45 and covers sampling opening 42. Filtering element 82 allows passage of gastrointestinal samples into collecting member 18 while preventing particles greater than the pore size to pass through filtering element 82 and therefore prevents fouling of sealing element 38.

In a further embodiment illustrated in FIG. 5*b*, filtering element 82 is external to covering element 30, which is seated external to sealing element 38, which in turn separates collecting member 18 from the outside environment. This configuration is advantageous in that covering element 30 which comprises a degradable material ruptures quickly as covering element 30 degrades and is not supported by filtering element 82. By rupturing quickly, covering element 30 allows rapid filling of collecting member 18 by gastrointestinal samples, thereby ensuring that a very specific location of the GI tract is sampled in a time period of less than 20 minutes. The pores of filtering element 82 allow passage of gastrointestinal samples into collecting member 18 while preventing particles greater than the pore size to pass through filtering element 82. This embodiment therefore prevents fouling of sealing element 38, shown here as a duck bill valve mounted in housing 45. The order of elements of device 10 in this embodiment, from the direction of gastrointestinal tract towards collecting member 18, is filtering element 82, covering element 30, sealing element 38 and collecting member 18.

In a further embodiment, filter element 82 is compressed axially and/or radially when dry and expands when exposed to fluids. Example materials of such a material comprise natural sponges and PVA open cell foams. By expanding when wet, filtering element 82 can help burst open or rupture the remaining portions of covering element 30 that have yet to degrade and thereby accelerate the rate of sampling. Furthermore, a compressed filtering element 82 makes for a more compact device 10 to ease swallowing by the user. Lastly, an expanding filtering element 82 increases the filtering surface area and effective pore size, thereby enabling a higher volume of sample to flow through into collecting member 18 before filtering element becomes clogged with particulate matter and mucus present in the gastrointestinal digesta.

In a further embodiment illustrated in FIG. 5*c*, filtering element 82 is coated or impregnated by covering element 30, which in turn block the pores or passageway of filtering element 82. This configuration is advantageous in that covering element 30 is mechanically supported by the structure of filtering element 82. Covering element 30, which comprises degradable material, degrades until the pores of filtering element 82 are exposed individually and allow passage of gastrointestinal samples into collecting member 18 while preventing particles greater than the pore size to pass through filtering element 82 and therefore prevents fouling of sealing element 38, shown here as a duck bill valve mounted in housing 45. Even if some of the pores of filtering element 82 become clogged with particles present in the gastrointestinal digesta, there will be other pores in filtering element 82 that are not clogged and will still let the liquid gastrointestinal samples through into collecting member 18. By way of example, if collecting member 18 can hold 100 microliters of sample and filtering element 82 comprises 100 pores, then each pore on average has to pass only 1 microliter of gastrointestinal samples before clogging in order to successfully fill the entire collecting member 18 with 100 microliters of gastrointestinal samples. In this embodiment, the rate of sample collection is determined by the rate degradation of covering element 30 which opens of the pores of filtering element 82 which in turn drives gastrointestinal samples 40 into collecting member 18 due to a lower pressure inside collecting member 18 relative to the GI tract being sampled.

In a further embodiment, the diameter of the pore size of filtering element 82 is used to control the lag time or degradation time of covering element 30. Larger diameter pores create a larger span of covering element 30, and hence a faster rupture of covering element 30 which leads to a shorter degradation or lag time. Smaller diameter pores provide better mechanical support for covering element 30 and hence a longer degradation or lag time. The diameter of the pores of filtering element 82 ranges from 500 microns down to 5 microns, with the lower limit set in order to enable microbes to be collected.

Figure 6:
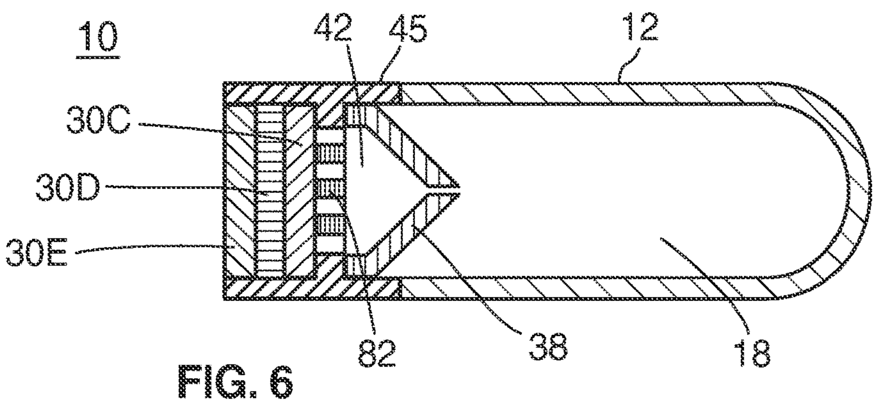
FIG. 6 illustrates a cross sectional view of the device comprising multiple covering elements.

In a further embodiment illustrated in FIG. 6, covering element 30*e* comprises an enteric degradable material that degrades at pH levels above 5, thus protecting covering element 30*d* from exposure to the GI fluids until after device 10 is in the duodenum. Covering element 30*d* comprises a rupturable material that is water-insoluble but water-permeable. Preferably, covering element 30*d* comprises a hydrophobic and relatively rigid polymer, so that the area under the stress-strain curve of a film made from the material of covering element 30*d* is between 0.005 to 0.4 mega Pascal.

In a further embodiment, the hydrophobic and rigid covering element 30*d* also comprises a hydrophilic polymer and/or a channel forming agent. Examples of such elements comprise hypromellose, calcium pectinate, calcium alginate, polyethylene glycol, polyethylene oxide and the like. The channel forming agent allows a controlled rate of water permeability through covering element 30*d* into the elements beneath. The channel forming agent also swells with water and weakens the rupture resistance of covering element 30*d*. The ratio of the hydrophobic and rigid polymer to the hydrophilic polymer and/or channel forming agent can be varied to control the lag time until covering element 30*d* ruptures. The thickness of covering element 30*d* can also be varied to control the lag time until covering element ruptures.

Element 30*c* comprises a swelling material that absorbs water permeating through covering elements 30*d*. At a certain time point, called the lag time, the swelling of element 30*c* ruptures covering element 30*d* and gastrointestinal samples 40 flow through filtering element 82, sampling opening 42, valve element 38, and into collecting member 18. The order of elements of device 10 in this embodiment, from the direction of gastrointestinal tract towards collecting member 18, is an enteric degradable covering element, a covering element comprising a rupturable material, a swelling element, filtering element 82, sealing element 38 and collecting member 18.

Figure 7:
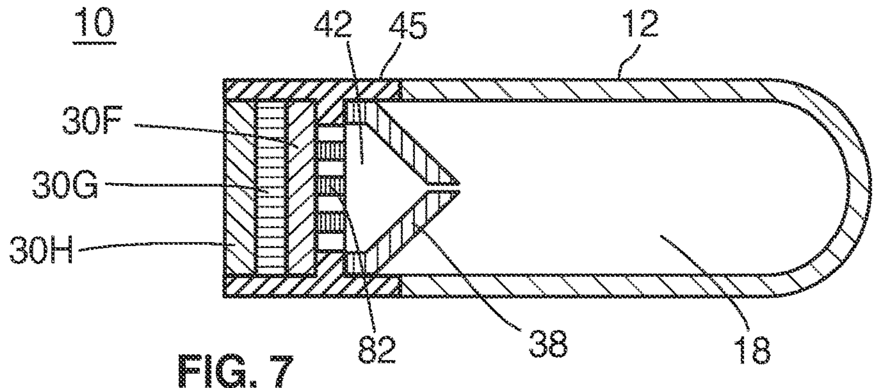
FIG. 7 illustrates a cross sectional view of the device comprising multiple covering elements.

In a further embodiment illustrated in FIG. 7, device 10 is configured to sample the ileum. Covering element 30*h* comprises a first enteric degradable material that degrades at pH levels above 5, thus protecting covering element 30*g* from exposure to the GI fluids of the stomach until after device 10 is out of the stomach and in the duodenum. Covering element 30*g* comprises a material that degrades at a rate that is independent of pH in the range of pH 5 to 8, thereby providing a lag time of up to 1 hour to allow device 10 to transit through the duodenum where pH levels can briefly reach pH 8 due to the localized release of bicarbonate in the duodenum that is used to neutralize stomach acid. Even brief exposure to fluids at pH levels above 7 would lead to premature degradation of covering element 30*f* and the inadvertent sampling of duodenal fluids. Covering element 30*g* therefore protects covering element 30*f* from exposure to the GI fluids of the duodenum until after device 10 is in the jejunum. Device 10 reaches the jejunum with covering element 30*f* intact. Covering element 30*f* comprises a second enteric degradable material that degrades at pH levels above 7 found in the ileum. Covering element 30*f* degrades in the ileum and gastrointestinal samples of the ileum are thus collected using this three layer covering element system. The order of elements of device 10 in this embodiment, from the direction of gastrointestinal tract towards collecting member 18, is a first enteric degradable covering element 30*h*, a pH independent degradable covering element 30*g*, a second enteric degradable covering element 30*f*, filtering element 82, sealing element 38 and collecting member 18.

In a further embodiment, device 10 with collapsed hollow body 12 is retained in the collapsed position inside soluble capsule shell 72. One or more of covering elements 30*a*-30*h* comprising pH dependent and pH independent materials, are coated or positioned on the outside surface of capsule shell 72 instead of covering sampling opening 42 directly. In this embodiment, hollow body 12 is transported through the GI tract in the compressed state due to the strength of capsule shell 72. At the intended sampling site, one or more covering elements 30*a-h* allow moisture to permeate, causing capsule shell 72 to degrade, which allows hollow body 12 to return to the expanded relaxed shape. The order of elements of device 10 in this embodiment, from the direction of gastrointestinal tract towards collecting member 18, is one or more of covering elements 30*a*-30*h*, soluble capsule shell 72, filtering element 82, valve element 38 and a collecting member 18. In this embodiment, covering elements 30*a-h* do not need to provide sufficient strength on their own to keep hollow body 12 compressed. Rather, covering elements 30*a-h* simply provide a moisture barrier that allows capsule shell 72, which is comprised of gelatin or HPMC, to remain dry and therefore maintain hollow body 12 in the compressed state.

In a further embodiment, covering element 30 provides sufficient strength to maintain hollow body 12 in the compressed state.

In a further embodiment, covering element 30 reduces the internal volume of hollow body 12 to less than 25%, or preferably less than 10% of the internal volume of hollow body 12 when relaxed. The elastic force of the collapsed, folded, twisted, and/or creased hollow body 12 trying to return to its natural relaxed shape helps to rupture covering element 30. When the strength of covering element 30 is sufficiently reduced by moisture, the elastic force trying to return hollow body 12 to is relaxed shape exceeds the retaining force of covering 30, and hollow body 12 resumes its natural relaxed shape while pulling in gastrointestinal samples.

Figure 8A:
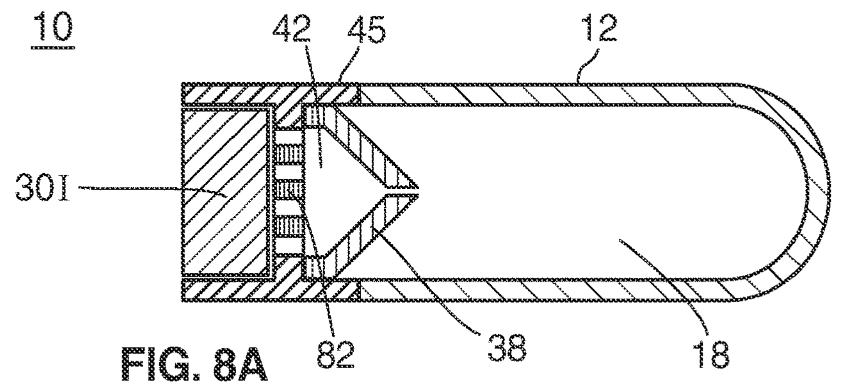
FIGS. 8*a-b* illustrate a cross sectional view of the device comprising a swellable plug covering element.
Figure 8B:
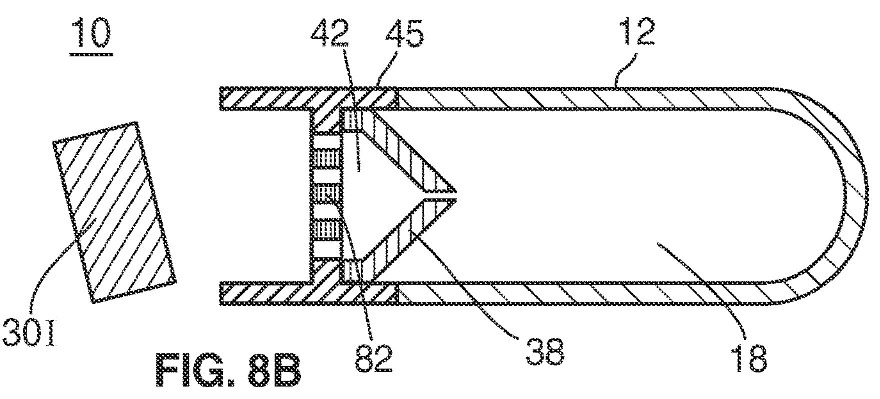

In a further embodiment illustrated in FIG. 8*a*, covering element 30*i* comprising a swellable material and functions as a plug that blocks sampling opening 42. When exposed to gastrointestinal fluids, covering element 30*i* starts to swell outwardly in the axial direction, as constrained by housing 45. Based on the swelling characteristics of covering element 30*i* and the geometry of fit between covering element 30*i* and housing 45, at a predetermined lag time, covering element 30*i* pops out of position and unblocks sampling opening 42, as illustrated in FIG. 26*c*. An example material for covering element 30*i* comprises compacted cellulose powder that swells when hydrated.

Covering element 30 can comprise multiple layers or sub-components, labelled as covering element 30*a* to covering element 30*i*. These layers or subcomponents can work together as a system to determine and initiate the sampling process. Covering elements 30*a*-30*i* can take the form of coatings, membranes, plugs, as well as structural components such as capsules, sleeves and collars that mechanically constrain hollow body 12 to a compressed, twisted, folded or kinked configuration.

In a further embodiment, covering element 30 is impinged and ruptured by a mechanical feature that is mounted on a swellable material. The mechanical feature comprises a sharp object that punctures covering element 30 after sufficient moisture causes swellable material to move in the direction of covering element 30. The time between initial moisture exposure of the swellable material to the puncturing of covering element 30 creates the desired lag time of sampling in the GI tract.

In a further embodiment, device 10 comprises a mechanical or electrical timing mechanism that activates sampling after a set lag time has elapsed post gastric emptying. The timing mechanism is exposed to moisture once a covering element comprising an enteric material degrades in the small intestine. The exposure to moisture initiates the timing mechanism so that the lag time until sampling only starts when device 10 arrives in the small intestine from the stomach.

In a further embodiment, sampling is triggered by sensing a decreasing partial pressure of oxygen in the gastrointestinal fluids that occurs in the ileum and ascending colon.

In a further embodiment, sampling is triggered by sensing an increasing partial pressure of hydrogen in the gastrointestinal fluids that occurs in the ileum and ascending colon.

In a further embodiment, device 10 comprises 2 filtering elements 82 of the same or differing pore size. The first filtering element 82 is positioned external to the second internal filtering element 82 which in turn is closer to collecting member 18. The pores of first external filtering element 82 are open and limit passage of particles to second internal filtering element 82 to a defined pore size or smaller. The second internal filtering element 82 is covered in covering element 30. As covering element 30 is degraded in the target region of the GI tract, pores of the second internal filtering 82 element open to allow the passage of gastrointestinal samples 40 into collecting member 18 due to a lower pressure inside collecting member 18 relative to the GI tract being sampled. However, without the first external filtering element 82, the rapid flow of gastrointestinal samples 40 through a small pore of the second internal filtering element 82 concentrates suspended particles in the bottleneck passageway of a pore and can block the pore due to the rapid agglomeration of suspended particles present in gastrointestinal samples 40. But in this embodiment, the flow going through the open pore in second internal filtering element 82 is diffused by the much larger surface area of the pores of first external filtering element 82. By way of example, if covering element 30 blocking a single pore of the second internal filtering element 82 opens to let in gastrointestinal samples 40, and assuming that first external filtering element 82 has 100 open pores, then the flow rate through each open pore of first external filtering element 82 is on average 1/100 the flow rate through the single open pore in second internal filtering element 82. Lower flow rates lead to a lower chance of fouling of the pores of first external filtering element 82. First external filtering element 82 acts as both a flow diffuser and pre-filter. Gastrointestinal samples 40 arriving at the second internal filtering element 82 have been pre-filtered by external filtering element 82 are devoid of particles of a size that can block the pores of the second internal filtering element 82, thereby allowing significantly more fluid to pass through into collecting member 18.

In a further embodiment, filtering element 82 comprises a sheath, sleeve of porous material that fits around at least some portion of hollow body 12 and sampling opening 42. An advantage of this embodiment is that the macroscopic surface area of filtering element 82 can be greater than the entire outside surface of hollow body 12, making it less likely that filtering element 82 will clog before collecting member 18 is completely filled with gastrointestinal samples. By way of example, filtering element 82 can be a porous mesh sleeve that is sealed on both ends and completely envelops or surrounds hollow body 12 and housing 45 like a sheath. Device 10, comprising this sheath-like filtering element 82 is placed into capsule shell 72.

In a further embodiment, filtering element 82 comprises a sheath or sleeve of porous material that fits around at least some portion of sampling opening 42 and/or housing 45 like a nose cone. The advantage of this embodiment is that the macroscopic surface area of filtering element 82 can be greater than the surface area of sample opening 42, making it less likely that filtering element 82 will clog before collecting member 18 is completely filled with gastrointestinal samples. By way of example, filtering element 82 can be a porous non-woven fiber mesh sleeve that is sealed around housing 45 and completely envelops sampling opening 42.

In a further embodiment, filtering element 82 comprises a semi-spherical dome or nose cone of porous material that fits in front of sampling opening 42. The advantage of this embodiment is that the macroscopic surface area of filtering element 82 is at least twice the surface area of sampling opening 42, making it less likely that filtering element 82 will clog before collecting member 18 is completely filled with gastrointestinal samples.

In a further embodiment, filtering element 82 comprises a thin sheet of porous material. The macroscopic surface area of filtering element 82 when laid out as a thin sheet is greater than 1 square centimeter, ignoring the surface area of the fibers or other microscopic structure that makes up the pore structure of filtering element 82. The surface area of 1 square centimeter or more assures that sufficient gastrointestinal fluids pass through filtering element 82 to fill collecting member 18 before clogging the pores of filtering element 82 or fouling sampling opening 42 or sealing element 38.

In a further embodiment, filtering element 82 comprises a thin sheet of porous material, and the macroscopic surface area of filtering element 82 when laid out as a thin sheet is 2 or more times the surface area of sampling opening 42, ignoring the surface area of the fibers or other microscopic structure that makes up pore structure of filtering element 82. The surface area of 2 or more times the surface area of sampling opening 42 assures that sufficient gastrointestinal fluids pass through filtering element 82 and through sampling opening 42 to fill collecting member 18 before clogging the pores of filtering element 82 or fouling sampling opening 42 or sealing element 38.

In a further embodiment, filtering element 82 comprises fibers that are packed together to create spaces for the sample to pass through.

In a further embodiment, the fibers of filtering element 82 are 1 to 100 microns in diameter.

In a further embodiment, the fibers of filtering element 82 are 10 to 50 microns in diameter.

In a further embodiment, the fibers of filtering element 82 are made of cellulose acetate.

In a further embodiment, the fibers, mesh or open pores of filtering element 82 are hydrophobic in order to prevent blocking or fouling of filtering element 82 by the particles and/or mucus contained in the gastrointestinal fluids. In this manner, flow through filtering element 82 is driven by a pressure differential created by an expanding hollow body 12, rather than by wicking forces or capillary action.

In a further embodiment, the diameter of the pore or opening size of filtering element 82 is 0.45 microns or less, preferably 0.22 microns or less, to allow only fluids through into collecting member 18 while not letting through microbes. The resulting collected gastrointestinal fluids collecting in device 10 are sterile in this embodiment, but might contain microbial fragments or viruses.

In a further embodiment, the diameter of a pore or opening size of filtering element 82 is 10 microns or less to allow only fluids containing microbes through into collecting member 18 while not letting though eukaryote cells which are generally larger than 10 microns in diameter.

In a further embodiment, the diameter of a pore or opening size of filtering element 82 is 25 microns or less to allow only fluids containing microbial and host cells through into collecting member 18, but not food particles which are generally larger than 25 microns in diameter. It is useful to collect epithelial host cells that are 10 to 20 microns in diameter for diagnostic and prognostic applications as described elsewhere herein. Food particles larger than 25 microns can foul filtering element 82, sampling opening 42 or sealing element 38.

In a further embodiment, the diameter of the pore or opening size of filtering element 82 is 50 microns or less to allow only fluids containing cells and small food particles through into collecting member 18 while not letting though food particles larger than 50 microns that can foul filtering element 82, sampling opening 42 or sealing element 38. Many microbes are present at highest numbers on the surface of food particles in the GI luminal digesta where the microbes are helping to break down the food. Therefore, by collecting small food particles into collecting member 18, the concentration of collected microbes and their metabolites is increased significantly.

In a further embodiment, filtering element 82 comprises consecutively reduced pore sizes with the smallest pores being positioned closest to sampling opening 42. The pores are in the range of 500 microns to 5 microns. By way of example, filtering element 82 comprises a set of 5 stacked polymer meshes with respective pore sizes of 250, 120, 60, 30 and 15 microns with the 15 micron filter being closest to sampling opening 42. This embodiment enables efficient sequential filtering and minimizes the likelihood of clogging filter element 82.

In another embodiment, the differential under pressure or vacuum generated by hollow body 12 is in the range of 0.5 to 4 pounds per square inch as measured across sampling openings 42 when hollow body 12 is in the fully collapsed state. It has been determined experimentally in vivo by the present inventor that at a pressure differential of greater than 4 pounds per square inch, the rapid inflow of gastrointestinal samples clogs filtering element 82 or sealing element 38 with flocculating food particles and debris. At a pressure differential of less than 0.5 pounds per square inch, there is insufficient pressure to crack open a one way valve sealing element 38, and therefore no sample is collected.

In another embodiment, actuator 24 actively forces sealing element 38 against sealing seat 39 with a pressure of at least 0.5 pounds per square inch with a sealing seat 39 surface area of less than 5 millimeters squared to affect a bacteria-tight seal even around any trapped particles, but only after the flow of gastrointestinal samples 40 into collecting member 18 is complete.

In a further embodiment, sampling opening 42 is wide-open with passageways with minimal resistance to flow, and not via a one way valve that is biased in the closed position. Only after collecting member 18 is filled in 20 minutes or less does actuator 24 move sealing element 38 against a sealing seat and actively create a seal.

In a further embodiment, actuator 24 is a polymer that swells when exposed to liquids.

In a further embodiment, sealing element 38 is a flutter valve, otherwise known as a Heimlich valve, made of two sheets of material laid flat against one another and attached at the edges. Gastrointestinal samples 40 travel through the flutter valve into collecting member 18 and cannot escape back out due to the pressure of the two sheets lying flat against each other.

In a further embodiment, at least 75%, preferably at least 85% and more preferably at least 90% of the collected gastrointestinal samples 40 inside collecting member 18 is stored as a free fluid and not contained as trapped fluid inside actuator 24. Free fluids are easier to extract for analysis relative to fluids contained within a swelling material. Analytes in free fluids are less likely to interact with the swellable polymeric material of actuator 24. In the event that actuator 24 is a foam-like material, then gastrointestinal samples 40 would be relatively easy to recover by squeezing the foam. However, hydrated foam is unlikely to apply sufficient and persistent axial force of 0.5 pounds per square inch or greater against sealing element 38 to create a seal tight enough to prevent entry of microbes or other objects that are as small as 0.22 microns. In the event that gastrointestinal samples 40 are mainly contained in a hydrogel-like material of actuator 24, then actuator 24 can apply considerable force on sealing element 38 against sealing seat 39 in order to create a microbe-tight seal, however gastrointestinal samples 40 will be very difficult to extract from the hydrogel material of actuator 24 given how strongly a hydrogel trap fluids. Therefore, it is advantageous to keep the vast majority of gastrointestinal fluids as a free fluid within device 10 and not contained in the swellable material of actuator 24.

The duration of sampling of 20 minutes or less is important as it controls how narrow of a region of the GI tract is sampled. The duration of sampling is defined as the time that sample crosses into sampling opening 42 until the time that sampling opening 42 is sealed by sealing element 38. The duration of sampling is governed by the expansion rate of the swelling material of actuator 24 and/or degradation of restraint 34 when exposed to fluid, and the distance between sealing element 38 and sealing seat 39. Even when fluid flow into collecting member 18 has ceased, the bacterial further down the GI tract can still enter collecting member 18. Therefore, it is important to seal sampling opening 42 tightly as soon after collecting member 18 is filled. Sealing too soon could cause sampling opening 42 to be sealed before gastrointestinal samples 40 have completely filled collecting member 18. By controlling the swelling rate of actuator 24 and the distance between sealing element 38 and sealing seat 39, a range for the sample duration can be set. In one embodiment, the sampling duration is 20 minutes or less. Therefore, assuming a gap of 0.5 mm between sealing element 38 and sealing seat 39, actuator 24 will expand in the axial direction at a minimal rate of 0.025 mm/minute.

In a further embodiment, actuator 24 also acts as sealing element 38. In this embodiment a single material performs both the actuator and sealing functions.

In a further embodiment, a thin walled tube comprises sampling opening 42. After the sample duration has elapsed, actuator 24 kinks the thin walled tube by bending the tube back on itself in a sharp curvature, thereby forming sealing element 38 in the form of a blocked lumen of a kinked tube.

Figure 9A:
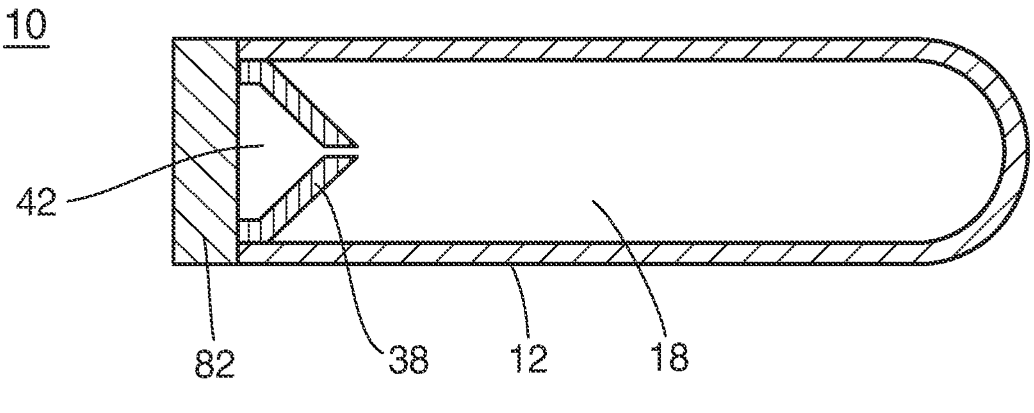
Figure 9B:
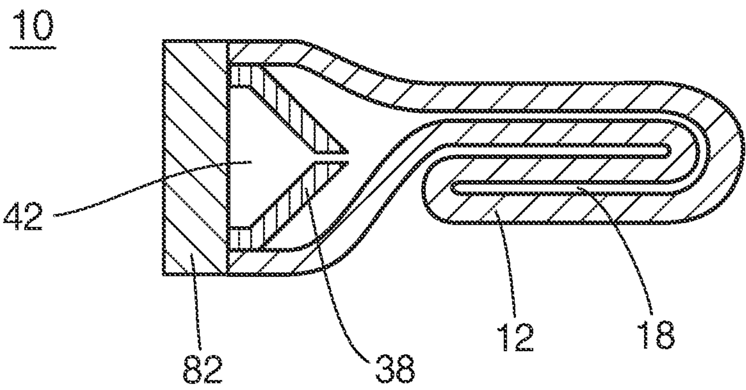
Figure 9B:
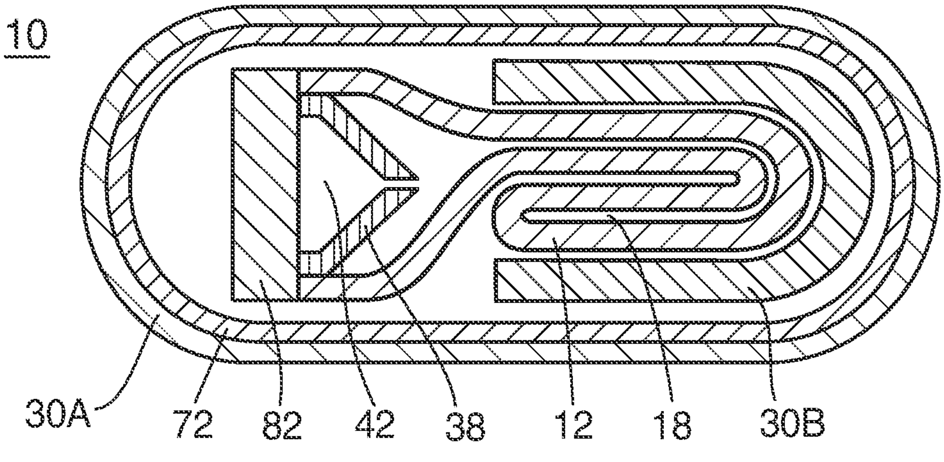
Figure 10:
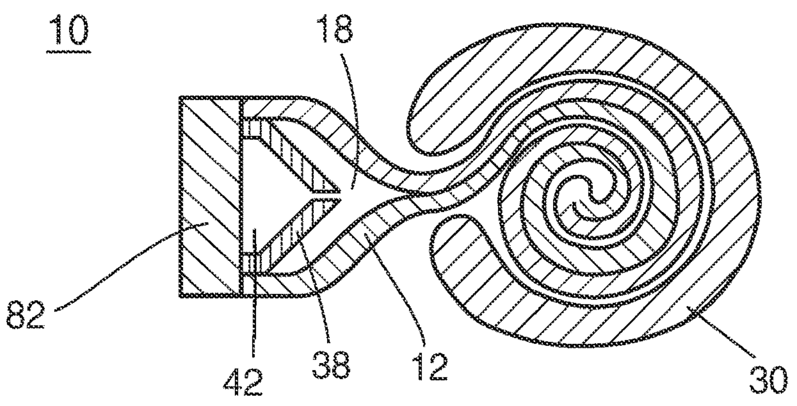
FIG. 10 illustrates a cross sectional view of the device in a spiral fold configuration with a c-shaped covering element.

In another aspect of the present invention, device 10 initiates sampling of a region of interest in the GI tract by a combination of pH and time dependent materials that degrade in a successive manner. In one embodiment, first covering element **30*a* comprises a material that degrades at a pH of 5 or higher, and second covering 30*b* element comprises a material that degrades at a rate that is independent of pH in the range of pH 5 to 8. Therefore, by varying the time required to degrade covering element 30*b* either by controlling the geometry or chemical composition of the material of covering element 30*b*, initiation of sampling can be set to begin after a known delay or lag time after swallowing of device 10. This two-stage, or double-trigger sampling embodiment illustrated in FIGS. 9*a*-9*c*. Device 10 is illustrated in FIG. 9*a* in the initial state where hollow body 12 is in the relaxed state. Filtering element 82 covers sampling opening 42. Sealing element 38, in the form of a one-way valve, separates sampling opening 42 from collecting member 18. Collecting member 18 is defined by the inside volume of hollow body 12**.

In FIG. **9*b*, in preparation for packaging, hollow body 12 is elastically compressed, and optionally folded, kinked, rolled, twisted and/or creased, thereby reducing the internal volume of hollow body 12 to less than 25%, or preferably less than 10% of the internal volume of hollow body 12 when relaxed. The internal volume of hollow body 12 is equivalent to collecting member 18. If not constrained, hollow body 12 will elastically revert to the relaxed and unfolded shape, and in the process gas or fluid will be sucked in through filter 82 through, sampling opening 42, and sealing element 38 into collecting member 18**.

In FIG. **9*c*, covering element 30*b*, in the form of a mechanical cap, retains hollow body 12 in the folded and compressed state thereby reducing the internal volume of hollow body 12 to less than 25%, or preferably less than 10% of the internal volume of hollow body 12 when relaxed. Capsule shell 72 surrounds covering element 30*b*. Covering element 30*a* is pH sensitive and covers capsule shell 72. Device 10** is ready for swallowing by the user in this configuration.

In the low pH environment of the stomach, covering element **30*a* protects capsule shell 72 and covering element 30*b* from contact with moisture. In the small intestines, covering element 30*a* degrades, thereby dissolving and degrading capsule shell 72, which in turn exposes covering element 30*b* to moisture. Covering element 30*b* starts to degrade in a time-dependent manner. When sufficiently degraded, covering element 30*b* loses the required mechanical hoop strength to prevent the elastic unfolding and radial expansion of hollow body 12. Since covering element 30*b* is not highly elastic, hollow body 12 will at some point snap to the unfolded state, which ensures that the sampling event happens in a discrete and defined amount of time of 20 minutes or less. Fast sampling ensures specificity of sampling location. Unfolding and expansion of device hollow body 12 draws gastrointestinal samples 40 into collecting member 18 through filtering element 82, sampling opening 42 and sealing element 38. Within 20 minutes from the time that hollow body 12 starts to unfold and/or expand due to sufficient degradation of covering element 30*b***, the sampling process is finished. Sampling of gastrointestinal fluids, therefore, is a rapid event that occurs within a 70 cm long stretch of the GI tract, allowing location specificity of the collected samples.

In a further embodiment, covering element **30*b* is a ring or collar that covers a portion of hollow body 12, but at the time of sampling initiation, covering element 30*b* does not cover the region of sampling opening 42. The advantage of the two embodiments above is that the material from covering element 30*b* does not cover sampling opening 42 at the time of sampling initiation and therefore does not interfere with the flow of gastrointestinal fluids into collecting member 18 at the moment when the sampling is triggered. If partially degraded remnants of covering element 30*b* are close to sampling opening 42, then portions of covering element 30*b* can get sucked against sampling opening 42 and block further ingress of gastrointestinal samples. Capsules shell 72 and covering elements 30*a* and 30*b* are fully dissolvable in the gastrointestinal tract within 12 hours of being swallowed. To minimize the chance of device retention in the GI tract, this embodiment leaves no solid objects inside the GI tract larger than hollow body 12 and filtering element 82**.

In a further embodiment, covering element **30*b* acts as a restraint to the axial, radial and/or rotational motion of an element that draws gastrointestinal samples into collecting member 18**.

In a further embodiment, covering element **30*b* completely envelopes hollow body 12 and filter element 82**.

In a further embodiment, a fill tube extends out from sampling opening 42. Before sampling, the fill tube is kinked and covering element **30*b* is a collar that maintains the fill tube in the kinked configuration. When covering element 30*b* degrades at the desired location in the GI tract, the fill tube unkinks and allows gastrointestinal samples to flow via sampling opening 42 into collecting member 18**.

In a further embodiment, hollow body 12 is configured as a long tube that is radially compressed in an elastic manner. Before sampling, one or more region of hollow body 12 are kinked and covering element **30*b* is a collar that maintains hollow body 12 in the kinked configuration. When covering element 30*b* degrades at the desired location in the GI tract, the hollow body 12 unkinks and allows gastrointestinal samples to flow via sampling opening 42 into that region of hollow body 12. By varying the pH or time required to degrade the plurality of covering elements 30*b* along hollow body 12, different regions of the gastrointestinal tract can be sampled in sequence and stored as a linear array inside hollow body 12**.

Three sources of variability in sampling from a specific region of the GI tract post swallowing are the variability of time that device 10 is retained in the stomach, the rate at which device 10 is moved through the small intestines, and the rate at which device 10 is moved through the colon. It is advantageous to eliminate the variability of gastric retention time from the overall targeting variability when trying to sample the small intestine or ascending colon. Therefore, in a further embodiment, covering element 30*a* comprises a pH-dependent moisture degradable material set to degrade at a pH above 5 that is present in the duodenum. In this manner, device 10 is delivered to the duodenum with covering element 30*a* intact, independent of how long device 10 stays in the low pH environment of the stomach. Degradation of covering element 30*a* in the duodenum exposes covering element 30*b* to moisture. Covering 30*b* comprises a pH-independent moisture degradable material which degrades at a predictable rate starting in the duodenum.

In one embodiment, capsule shell 72 comprises enteric covering element 30*a* which delivers device 10 into the duodenum when hollow body 12 is still folded up inside capsule shell 72. In the folded state, the internal volume of hollow body 12 is less than 25%, or preferably less than 10% of the internal volume of hollow body 12 when relaxed. In the small intestines, covering element 30*a* and capsule shell 72 degrade. Covering element 30*b* still blocks sampling opening 42 or restrains hollow body 12 from unfolding or expanding, thereby preventing gastrointestinal fluids from flowing into collecting member 18. Device 10 travels through at least a portion of the small intestine in this configuration. When covering element 30*b* degrades, gastrointestinal fluids flow through sampling opening 42 in collecting member 18.

In one embodiment, covering element 30*b* comprises a polymer that erodes in aqueous environments in a layer thickness of 0.1 to 5.0 mm, where the layer thickness of covering element 30*b* determines the lag time until sampling initiation.

In a further embodiment, covering element 30*b* comprises a polymer that erodes in aqueous environments, for example partially cross-linked hydroxypropyl cellulose, where the extent of cross-linking of covering element 30*b* determines the lag time until sampling initiation.

Transit time of device 10 through the small intestines takes 2 to 5 hours on average. There is an increasing gradient of pH along the small intestine rising towards a pH of 6.6 (+/−0.5 pH units) in the jejunum, to 7.5 (+/−0.5 pH) units in the ileum, which is used by enteric release agents to target the jejunum and ileum regions. However this pH gradient can vary significantly among individuals, and within the same individual based on diet and time of day. The pH gradient is not sufficiently predictable to robustly target the jejunum and ileum at all times of the day and based on all diet types. Furthermore, the degradation property of pH dependent materials is highly non-linear with significantly higher degradation times in just slightly higher pH levels. Therefore, it is advantageous to initiate the sampling event in the jejunum, ileum or colon based on a predictable transit time delay after the device has reached the duodenum, instead of basing the sampling on a predicted pH gradient along the small intestines. In this embodiment, adjusting the degradation time of covering element 30*b* controls how far into the small intestine or colon device 10 will reach before initiating the sampling event. By way of example, covering element 30*a* that degrades in the duodenum at a pH level of 5 or higher coupled with covering element 30*b* that degrades after 1 to 2 hours will reliably sample the jejunum. Likewise, covering element 30*a* that degrades in the duodenum at a pH level of 5 or higher coupled with covering element 30*b* that degrades after 2 to 5 hours will reliably sample the ileum. Finally covering element 30*a* that degrades in the duodenum at a pH level of 5 or higher coupled with covering element 30*b* that degrades after 5 hours will reliably sample the ascending colon.

In a similar embodiment, covering elements 30*a* can be targeted to the pH of the jejunum. By way of example, covering element 30*a* that degrades in the jejunum at a pH level of 6.5 or higher coupled with covering element 30*b* that degrades after 1 to 2 hours will reliably sample the ileum. Likewise, covering element 30*a* that degrades in the jejunum at a pH level of 6.5 or higher coupled with covering element 30*b* that degrades after 2 to 4 hours will reliably sample the ascending colon.

In a similar embodiment, covering elements 30*a* can be targeted to the pH of the ileum. By way of example, covering element 30*a* that degrades in the ileum at a pH of 7 or higher coupled with covering element 30*b* that degrades after 1 to 2 hours will reliably sample the ascending colon. This last embodiment is particularly useful since the pH of the ascending colon generally drops relative to the pH of the ileum. This pH drop makes it difficult to target using an enteric degradable material. If the enteric coating is too thin or dissolves too quickly in high pH levels of the ileum, the enteric coating would degrade prior to entering the lower pH environment of the ascending colon. On the other hand, if the enteric coating degraded slowly enough to survive intact in the high pH of the ileum and enter the ascending colon, the coating would likely not be degraded further in the lower pH levels of the colon relative to the ileum. Therefore, a two-stage targeting approach is preferred for targeting specific regions of the GI, where the first stage of degradation targets a minimum pH level and the second stage of degradation is based on time in a pH-independent manner. Furthermore, the device and methods disclosed here do not rely on region-specific gut microflora that may or may not be present in order to degrade the covering element.

In a further embodiment, the first covering element is enteric degradable material that degrades at a pH of greater than 5 as found in the duodenum to expose a second covering element. The second covering element is pH independent and degrades after a delay of up to one hour, at which point device 10 has left the duodenum and entered into the jejunum. The degradation of the second pH independent covering element exposes a third covering element comprising an enteric degradable material that degrades at a pH level of greater than 6 to sample from the jejunum or ileum. The advantage of this approach is that the present inventor has discovered experimentally that the pH levels of certain regions of duodenum can momentarily range from pH 3 to pH 8 due to imperfect mixing and the pulsative release of the alkaline and acidic substances into the duodenum. A high pH environment, even momentarily, can rapidly and non-linearly degrade enteric covering elements and can cause premature sample collection. By comprising a pH independent moisture degradable material, the second covering element gives device 10 sufficient time to transition into the more stable and predictable pH gradient present in the jejunum and ileum. Sampling is triggered by degradation of the third covering element in a more predictable manner, since this third covering element was not prematurely degraded by regions of very high pH in the duodenum.

Typical enteric delivery systems involve a coating of a pH dependent enteric degradable material on top of a capsule shell made from gelatin or hypromellose, which are materials that degrade in a pH-independent manner. However, these underlying pH-independent materials are not intended to substantially delay the delivery or targeting of an active agent after degradation of the enteric coating. The degradation of such thin films of approximately 0.1 to 0.2 mm thickness of gelatin or hypromellose (HPMC) capsules typically occurs within a few minutes. The pH-independent capsule shell serves simply as a substrate for the application of the enteric coating, which is the main targeting agent in these systems. The covering element comprising pH-independent materials of the present invention degrades at time scale of 20 minutes or more after exposure to moisture to enable device 10 to transition to a downstream region of the GI tract before initiating sampling.

Figure 2A:
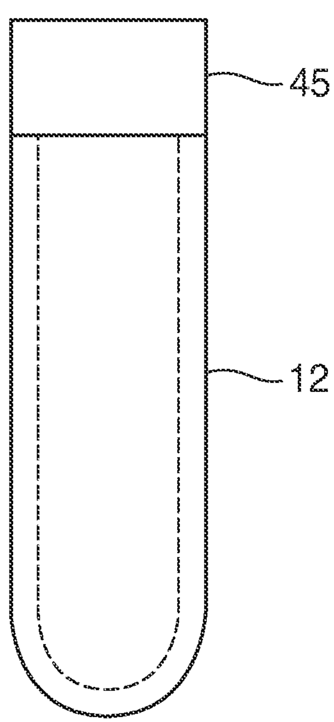
FIGS. 2*a-d* illustrate a folding pattern of the hollow body of the device prior to insertion into a capsule shell or covering element.
Figure 2B:
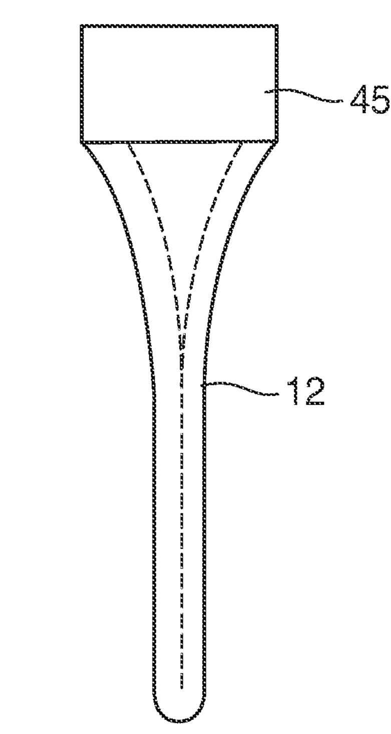
Figure 2C:
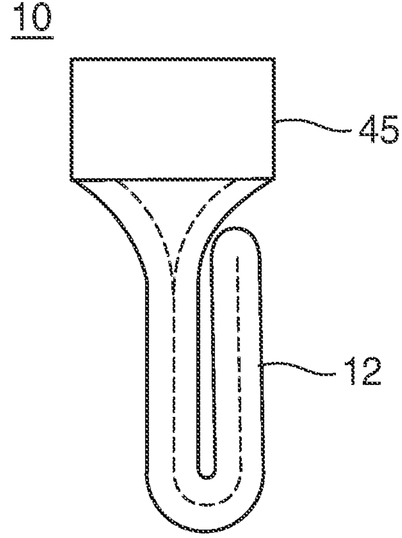
Figure 2D:
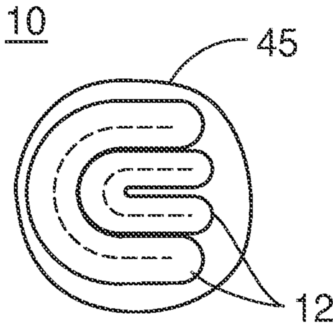

In a further embodiment, device 10 comprises a radially-collapsed thin-walled tubular-shaped hollow body 12 that is folded up onto itself and then creased along the long axis to fit inside an external capsule shell 72 and/or covering element 30. FIG. 2*a* depicts a side view of device 10 comprising housing 45 and a thin-walled tubular-shaped hollow body 12 in the natural relaxed configuration. FIG. 2*b* depicts a side view of device 10 comprising a radially collapsed thin-walled tubular-shaped hollow body 12 in a flattened configuration. FIG. 2*c* depicts a side view of device 10 after the first axial fold where hollow body 12 is folded up onto itself. FIG. 2*d* depicts a mid-height cross section view of device 10 after the second crease fold of hollow body 12 prior to insertion into capsule shell 72 and/or covering element 30 in preparation for swallowing by a subject. Note that the hollow body 12 is nested within itself with one portion of hollow body 12 being on the outside and a second portion of hollow body 12 being on the inside of the nesting arrangement. The internal volume of hollow body 12 when folded is less than 25%, or preferably less than 10% of the internal volume of hollow body 12 when relaxed. The advantages of this folding configuration are the minimization of bactericidal oxygen inside collecting member 18, are the shortening of hollow body 12 making it easier to swallow, and the minimization of dead space inside the capsule shell that is swallowed by the subject. Furthermore, no axial expansion mechanism, such as accordion pleats, sliding seals or invagination, is required to convert a compactly package device 10 into a fully expanded hollow body 12 configuration.

Figure 3A:
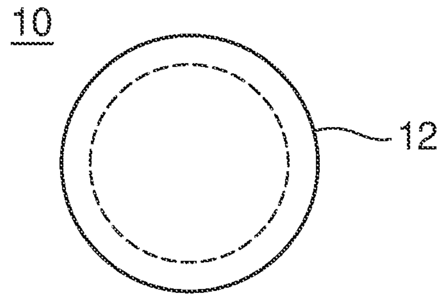
FIGS. 3*a-d* illustrate a folding pattern of the hollow body of the device prior to insertion into a capsule shell or covering element.
Figure 3B:
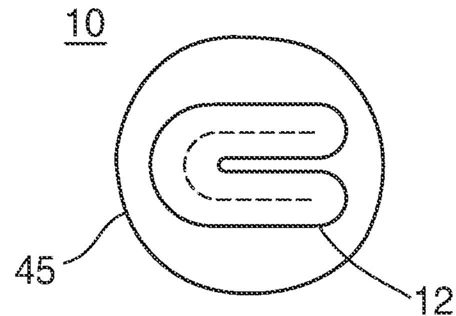
Figure 3C:
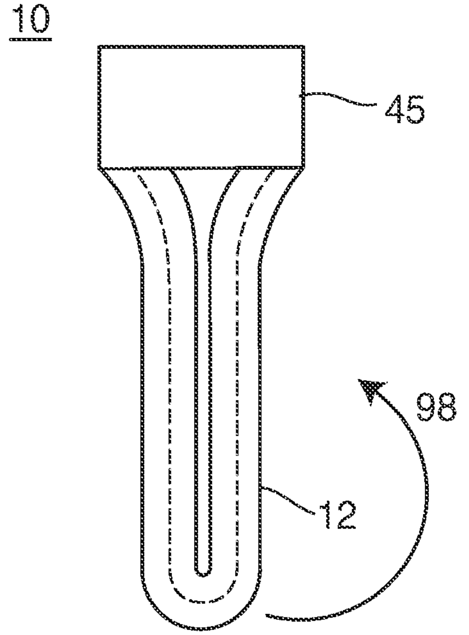
Figure 3D:
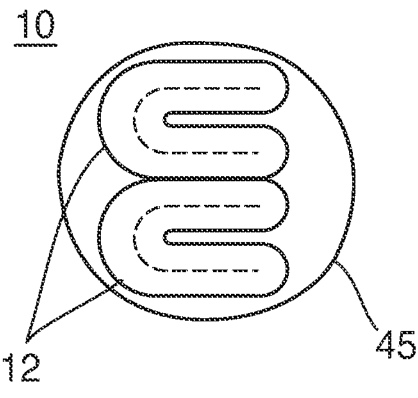

In a further embodiment, device 10 comprises a radially-collapsed thin-walled tubular-shaped hollow body 12 that is first creased along the long axis and then folded axially to fit inside an external capsule shell. FIG. 3*a* depicts a bottom end view of device 10 comprising a thin-walled tubular-shaped hollow body 12 in the natural relaxed configuration. FIG. 3*b* depicts a mid-height sectional view of device 10 comprising a radially collapsed thin-walled tubular-shaped hollow body 12 which takes a flat configuration that is creased along the long axis. FIG. 3*c* depicts a side view of device 10 after the first crease fold depicted in FIG. 3*b*. FIG. 3*d* depicts a mid-height sectional view of device 10 after the fold along the long axis of hollow body 12 in the direction of arrow 98 in FIG. 3*c* prior to insertion into an external capsule shell in preparation for swallowing by a subject. Note that the hollow body 12 runs along itself in a parallel fashion with one portion of hollow body 12 being on one side of a central plane and a second portion of hollow body 12 being on the other side of a central plane. The advantages of this folding configuration are the shortening of hollow body 12 making it easier to swallow, and the minimization of dead space inside the capsule shell that is swallowed by the subject. Furthermore, no axial expansion mechanism, such as accordion pleats, sliding seals, or invagination, is required to convert a compactly package device 10 into a fully expanded hollow body 12 configuration.

Figure 4A:
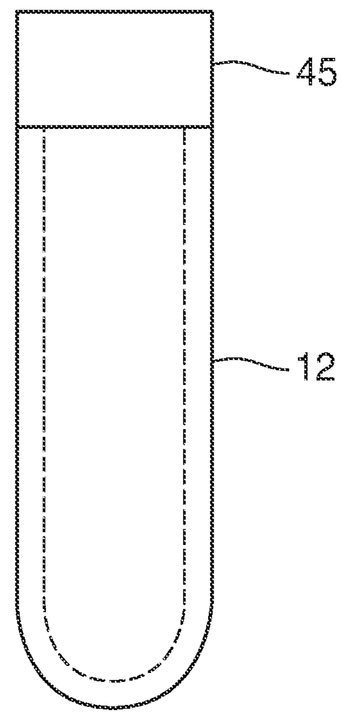
FIGS. 4*a-c* illustrate a folding pattern of the hollow body of the device prior to and after insertion into a capsule shell or covering element.
Figure 4B:
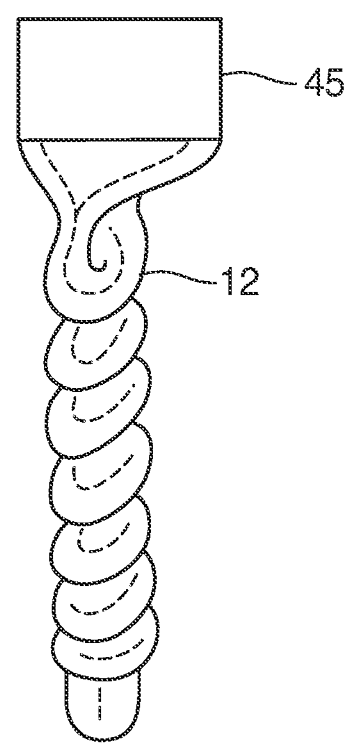

In a further embodiment, device 10 comprises a radially-collapsed thin-walled tubular-shaped hollow body 12 that is twisted axially and then folded up onto itself along the long axis to fit inside an external capsule shell. FIG. 4*a* depicts a side view of device 10 comprising housing 45 and a thin-walled tubular-shaped hollow body 12 in the natural relaxed configuration. FIG. 4*b* depicts a side view of device 10 comprising a radially collapsed thin-walled tubular-shaped hollow body 12 twisted along the long axis in order to evacuate and collapse the inner volume of tubular-shaped hollow body 12. Hollow body 12 is inserted into an external capsule shell 72 and/or covering element 30 in this state. The external capsule or covering element prevents the unfolding of hollow body 12 until the desired location of the GI tract is reached.

In a further embodiment, FIG. 3*c* depicts a side view of device 10 after folding twisted hollow body 12 along the long axis to shorten the overall length of hollow body 12 even further to around half of the original relaxed length. FIG. 3*c* depicts device 10 after inserted in the twisted and folded configuration into an external capsule shell 72 and/or covering element 30 in preparation for swallowing by a subject. The twisting and folding pattern disclosed herein both evacuates hollow body 12 in preparation for sample collection, and also shortens device hollow body 12 so that device 10 fits into a standard-shaped sized capsule shell 72. The advantage of this folding configuration is the minimization of dead space inside the capsule shell that is swallowed by the subject. Furthermore, no axial expansion mechanism, such as accordion pleats, sliding seals, or invagination, is required to convert a compactly package device 10 into a fully expanded hollow body 12 configuration.

Figure 4C:
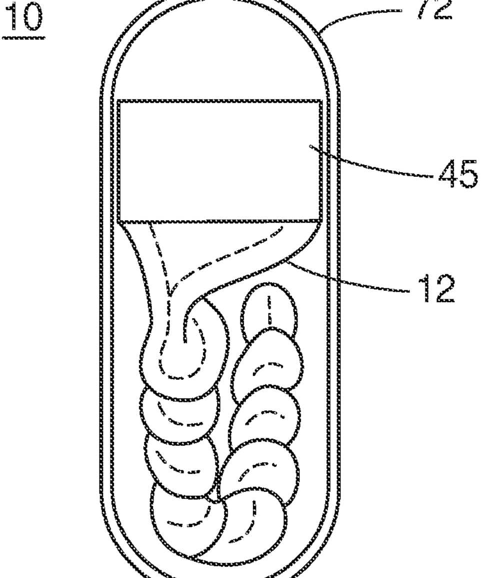

In a further embodiment, combinations of folds and packaging configurations such as those disclosed in FIGS. 2, 3 and 4 are used to package device 10 prior to insertion into capsule shell 72 and/or covering element 30 for swallowing by the subject.

In a further embodiment, capsule shell 72 or covering element 30 used to package compacted device 10 is less than two thirds, or preferably less than one half, the length of device 10 when hollow body 12 is in the relaxed and unfolded state. The increase in length of device 10 is obtained by untwisting, uncompressing or unfolding of hollow body 12, which did not undergo invagination or other forms of axial expansion.

In a further embodiment, moisture or liquid water entering device 10 activates a chemical reaction whose output is gas. The gas pressure generated by the chemical reaction acts as actuator 24 to displace sealing element 38 and seal sampling opening 42 or to reinforce the sealing capability of sealing element 38.

In a further embodiment, high pressure gas is trapped as little bubbles inside a degradable material within hollow body 12. As the degradable material degrades due to the presence of gastrointestinal samples inside collecting member 18, the gas is released and builds up pressure inside collecting member 18 that acts to seal or reinforce the sealing capability of sealing element 38.

In a further embodiment, gastrointestinal samples 40 or a separate moisture reservoir hydrate a sealing material that hardens, crosslinks, expands or polymerizes once hydrated. The hardening, crosslinking, expansion or polymerization of the sealing material seals collecting member 18.

In another embodiment, collecting member 18 comprises a preservation agent or agents in the dry, solid, powder, crystalline, gel or freeze dried state. The advantage of placing the preservation agents inside device 10 in the dry, solid, powder, crystalline or freeze dried form is better shelf life of the preservation agent, lower volume of the empty collecting member 18 is taken up by the preservation agent relative to the solution form, and lack of interference of any moisture from a solution-based preservative with the moisture degradable materials inside device 10 during use and storage. In order to minimize the dead volume of device 10, and maximize the ability of the preservation agent to mix and dissolve within the free fluids collected in collecting member 18, the dry, solid, powder, crystalline, gel or freeze dried preservation agent is placed loosely in the empty collecting member 18 with no carrier or holding element such as foam. Since many of the preservation agents are hard to get into solution at the required concentrations (for example ammonium sulfate is required at 10 g/100 ml in order to preserve RNA) the dry, solid, powder, crystalline or freeze dried preservation agent can thus slosh around as device 10 moves through the GI tract in order to more uniformly disperse and solubilize the preservation agent within the collected gastrointestinal samples 40. The relative motion of the sample and the preservation agent is not possible if the preservation agent and the samples are held inside device 10 by a carrier element such as a sponge. The collected gastrointestinal samples 40 provide the needed moisture for rehydrating the preservation agent. The preservation agents help stop all enzymatic activity and preserve microbial cells, analytes, DNA, RNA and/or proteins in the collected gastrointestinal samples for further analysis outside the hollow body. Example preservation agents comprise ethylenediaminetetraacetic acid (EDTA), sodium citrate dehydrate, ammonium sulfate, cesium sulfate, DNAse inhibitor, RNase inhibitor, sorbic acid, citric acid, propyl paraben, nisin, dimethyl dicarbonate, sodium azide, hydroxyurea, fusidic acid, diazolidinyl urea, imidazolidinyl urea, salicylic acid, barium and nickle chloride, metallic copper, thimerosal, 2-phenoxyethanol, and the like. The preservation agents will be hydrated by the gastrointestinal samples 40 entering into collecting member 18. Sufficient amounts of the preservation agents will go into solution to have desired preservation effect on the collected gastrointestinal samples 40, with the remaining preservation agents remaining solids inside collecting member 18. A target range of salt to add for a collection capsule with a 0.5 ml capacity is 10 to 250 milligrams.

In another embodiment, device 10 comprises a moisture sensor that detects the presence of a fluid inside covering member 30 or inside collecting member 18. A signal is sent to a receiving unit at the time of sampling or passage of device through a specific GI tract landmark. By way of example, a first moisture sensor is placed inside pH sensitive covering member 30*a* that degrades at pH 5 or greater, and a second moisture sensor is placed inside collecting member 18. Gastrointestinal samples pass into collecting member 18 based on the time-dependent degradation of covering element 30*b* that begins to degrade after gastric emptying. In this example, a first signal from the first moisture sensor is transmitted when device 10 passes through the pylorus into the duodenum during gastric emptying. A second signal from the second moisture sensor is transmitted when device 10 moves along inside the intestines due to natural peristalsis for a set time interval based on the degradation properties of covering element 30*b*. In this manner, the location of sampling is calculated by the time difference between the two signals multiplied by the average small intestine transit time of 200 cm per hour. If the time difference between the two signals is 2 hours, then device 10 sampled at around 400 cm after the pylorus, which is the ileum region of the small intestine.

In a further embodiment, the moisture sensor in the embodiment above stops transmitting a signal when moisture is present. An example of such a sensor comprises a radio frequency identification (RFID) tag whose antenna or other electrical component cease functioning at their normal levels when exposed to liquid.

In another embodiment, device 10 comprises a temperature sensor that detects the temperature inside device 10. Device 10 further comprises a chemical agent that undergoes an exothermic reaction for a predefined period of time when exposed to moisture. In this manner, when moisture reaches an internal portion of device 10, as in the preceding example, an exothermic reaction occurs for a set time period that increases the temperature of the temperature sensor. A signal indicating the increase in temperature is sent to a receiving unit indicating the presence of moisture in that portion of device 10. As in the example above, a first moisture-sensitive heat generating chemical agent can be placed inside pH sensitive covering member 30*a* that degrades at pH 5 or greater, and a second moisture-sensitive heat generating chemical agent is placed inside collecting member 18. Both chemical agents are in proximity to a single temperature sensor that wirelessly transmits temperature to a receiving unit. The location and time of sampling are determined by determining the intervening time between the two signals, as per the preceding example. Example of temperature sensing devices comprise temperature sensing RFID tags. Example moisture sensitive exothermic chemical agents comprise magnesium.

In another embodiment, human cells, human proteins or RNA transcripts in the sample are used to determine the sampling location. By way of example, colonic epithelial cells should not be present in a small intestine sample. Likewise, small intestine epithelial cells should not be in a stomach sample. The furthest downstream human cell type in a sample is used to define the sampling location of device in the GI tract.

It has been experimentally determined by the present inventor that the same type of device 10 with the same type of covering element 30 will sample entirely different regions of the GI tract and collect samples of different pH levels depending on when device 10 was swallowed in relation to the consumption of food. In this embodiment, instead of targeting different regions of the GI tract with different type covering elements 30 each degrading after a set time of degradation or in a predetermined pH range, a single type of device 10 with a single type of covering element 30 can be used to target different regions of the small intestines or colon by speeding up or slowing down the peristalsis that occurs before, during and after the ingestion of food.

By way of example, device 10 comprising a covering element 30 that is designed to trigger sampling one hour after entering the duodenum will sample the jejunum if peristalsis is slow. The same device 10 will sample the ileum if the peristalsis is fast.

The transit of devices through the small intestine occurs at rate of highly variable speeds due to two different kinds of peristaltic waves. The peristaltic waves in the fed state move a device through the small intestine at around 0.3 to 2 cm per minute, whereas the peristaltic waves that occur at the end of the fed state, known as the phase III migrating motor complex, move objects along at a speed of around 5 to 20 cm per minute. The fed state usually lasts for around 25 to 35 minutes per 100 kilocalories of solid food ingested before the triggering of the phase III migrating motor complex at the end of the fed state. Furthermore, indigestible objects such as device 10 are usually emptied from the stomach only at the end of the fed state during the phase III migrating motor complex as part of a lumen-clearing housekeeping function. Therefore, irrespective of whether device 10 is swallowed right at the beginning, during, or right after a meal, device 10 will only be emptied from the stomach and into the small intestine when nearly all of the food has already been emptied from the stomach. The phase III migrating motor complex signifies the end of the fed state. Solid indigestible objects are usually retained in the stomach during digestion until the end of the fed state when they are propelled forward at relatively high speed of 5 to 20 cm per minute through the first part of the small intestine.

Most bacteria multiply with a 20-minute doubling time only when nutrients are present. By the end of 2.5 hours when an average 500 kilocalorie meal is fully digested and emptied from the stomach, the bacteria have had time for 7 to 8 doubling times, thereby increasing the numbers of bacteria considerable relative to the fasted state when much fewer nutrients are present in the small intestines. If the goal of device 10 is to sample the microbiota and their associated metabolites of the small intestine, it is advantageous to do so at the end of the fed state when the bacteria have had time to multiply and process the nutrients into the various metabolites.

Additionally, the pH of the stomach rises to 3, 4 or even 5 when food is ingested and only drops to pH of 1 or so an hour before the end of the fed state. If device 10 comprises an enteric coating that degrades at around pH 5 or higher, the enteric coating could be compromised by the relatively high pH of the stomach during the fed state.

Therefore, in order to collect as many small intestine bacteria as possible, and to minimize the time spent in the stomach during the fed state, device 10 is swallowed at a time point as close to the end of the fed state as possible. The number of kilo calories eaten is divided by the ratio range of 3 to 4 kilo calories per minutes in order to calculate the ideal time to swallow device 10. By way of example, after a 500 kilocalorie meal, the ideal time to swallow device 10 is in the window of 125 to 167 minutes, or roughly 2 to 3 hours, after the ingestion of the meal. Blended food or liquids will empty from the stomach much faster due to the lack of a lag time that the stomach needs to liquefy solid foods.

In a further embodiment, device 10 is swallowed within a time range after ingestion of solid food that is calculated as dividing the number of kilocalories eaten by the ratios of 1 kilo calorie per minute and 5 kilo calories per minute, or preferably the ratios of 3 kilo calories per minute and 4 kilo calories per minute.

The rate of passage of device 10 through the small intestine is controlled by the timing, quantity and type of food ingested once device 10 has passed into the small intestines. In a further embodiment, a method of speeding up the rate of passage of a device through the small intestines comprises ingesting a first meal of between 50 to 250 kilocalories, swallowing the device, waiting for the device to transition into the duodenum and the stomach to empty, and then eating a second meal of between 25 to 100 kilocalories to trigger an additional cycle of a phase III migrating motor complex within 2 hours following said second meal, thereby speeding up a rate of passage of the device 10 through the small intestines.

In a further embodiment, the first or second meal is blended in order to reduce gastric emptying time.

In a further embodiment, the meal above ingested again at least once following a delay of 0.5 to 2 hours. By ingesting small meals of blended food, the stomach transitions from fed state to fasted state quickly and repeatedly, which triggers additional phase III migrating motor complexes that clear the lumen and move all items, including device 10, at a speed of 5 to 20 cm per minute through the small intestines. Traveling through the small intestines at a faster rate makes it easier to target the distal regions, such as the terminal ileum and ascending colon, with one or more device 10.

In a further embodiment, a method of slowing down up the rate of passage of a device through the small intestines comprises ingesting a first meal of between 50 to 500 kilocalories, swallowing the device, waiting for the device to transition to the duodenum, and eating a second meal of between 100 to 700 kilocalories to delay onset of a phase III migrating motor complex for at least 2 hours following said second meal, thereby slowing down a rate of passage of the device through the small intestines. In this manner, the peristaltic waves in the small intestine are typical of the fed state and move all items, including device 10, at a speed of 0.3 to 2 cm per minute through the small intestines. Traveling through the small intestines at a slower rate helps increase the spatial resolution of the sampling of one or more device 10.

In a further embodiment, the user is instructed to wait at least 1 hour after eating a first meal for the stomach to become acidic before swallowing device 10 that comprises a pH dependent covering element 30.

In a further embodiment, device 10 comprises at least one covering element that includes material that degrades in a pH dependent manner.

In a further embodiment, device 10 comprises at least one covering element that includes material that degrades at a rate that is independent of pH in the range of pH 5 to 8.

In a further embodiment, the user is instructed to wait 1 to 2 hours after swallowing device 10 before ingesting a second meal in order to give time for device 10 to transition into the small intestines.

In a further embodiment, the timing of swallowing of device 10 or of ingesting the second meal after swallowing device 10 is determined based on the detection of a phase III migrating motor complex in a gastrointestinal tract.

The phase III migrating motor complex is heard as the sound that a rumbling stomach makes when a person is hungry after a meal. In a further embodiment, the detection of a phase III migrating motor complex is audible.

In a further embodiment, the food ingested in the method above has a defined content and balance of carbohydrates, fats and proteins in the range of 100% to 0% of all three components.

In a further embodiment, the methods above are repeated at least once with an interval of at least 4 hours apart, wherein the food consumed in the first repetition differs by at least 20% in the relative proportions of carbohydrates, fats and proteins as compared to the food consumed in the second repetition. In this manner, the response of the subject to all the three major dietary components can be assessed in a single day.

In a further embodiment, device 10 is used to collect cells, biomolecules or other biomarkers that can be used to detect, diagnose, prognose or track the treatment a condition or disease. Traditionally, in cancer for example, a liquid biopsy is a test done on a sample of blood to look for cancer cells from a tumor that are circulating in the blood or for pieces of nucleic acids from tumor cells that are in the blood. A liquid biopsy may be used to help find cancer at an early stage. Liquid biopsies are generally confined to blood, saliva, urine or cerebrospinal fluid. All of these bodily fluids are generally homogenous regardless of where and how the body fluid is obtained. In contract, the gastrointestinal fluids present in the GI tract vary widely in their composition depending across the different regions of the GI tract. This inhomogeneity is reflected in the diverse biochemical and physiological functions performed by the different regions of the GI tract.

Since the majority of deadly GI-related cancers are adenocarcinomas which are malignant tumors formed from glandular structures in epithelial tissue, many of the denuded cells of interest or molecular signature molecules such as nucleic acids and secreted compounds are present in the GI tract. There is a clear need to capture these cells, nucleic acids and other biomolecules in-situ and transfer them out of the body for further analysis as valuable cytology samples or biomarkers. However, the GI tract is relatively un-accessible without invasive or semi-invasive procedures such as biopsy and endoscopy. Device 10, however, traverses the GI tract and collects cells and biomolecules of interest for advanced diagnostic procedures from all regions of the GI tract and keeps them separated as discrete region-specific samples.

In a further embodiment, a subject swallows device 10 that is designed to sample in a specific region of the GI tract based on a pH range of that region and/or based on a known range of transit times to reach that region. The location of sampling of the collected cells or biomolecules is imputed by one or more of the position identification parameters comprising pH, color, microbial content, dissolved gases, metabolites, enzymes that are indicative of that region, or by region-specific histological markers on the collected denuded cells. A biomarker analysis is conducted on the collected sample. Example biomarkers include proteins, peptides, primary or secondary metabolites, circulating tumor cells (CTCs), cell-free DNA (cfDNA), circulating tumor DNA (ctDNA), epigenetic changes, methylation profile of DNA, histone acetylation state, microsatellite instability, chromosomal instability, programmed cell death-ligand 1 (PD-L1) status, micro RNA, cell-free RNA, cell-derived vesicles, such as exosomes, microbes, and viruses.

In a further embodiment, samples collected by device 10 are subject to analyses comprising the detection of the bacteria, viral and parasitic pathogens in patients with symptoms of infectious colitis or gastroenteritis, cytologic evaluation, genetic testing such as BRAF mutation analysis, HER2 fluorescent in-situ hybridization analysis, KRAS mutation analysis, aberrant NDRG4 and BMP3 methylation, β-actin, hemoglobin immunoassay and microsatellite instability testing (MSI).

In a further embodiment, the entire nucleic acid complement collected by device 10 is processed such that the nucleic acid originating from the host is isolated from the nucleic acid originating from GI microbes prior to sequencing the collected nucleic acid.

In a further embodiment, the GI luminal contents collected by device 10 are centrifuged to pellet the intact microbial and host cells and the supernatant containing cell free nucleic acids is isolated and the nucleic acids therein are sequenced. In this manner, the sequencing sample is significantly enriched for cell free host nucleic acid relative to the much larger amount of nucleic acids present in intact host and microbial cells. The cell free nucleic acids are useful in the diagnostic and prognostic procedures disclosed elsewhere in this patent. Hosts comprise mammals such as humans. A range of centrifugation speeds and times comprise 5,000-30,000 RCF for 1 to 5 minutes.

In a further embodiment, the GI luminal contents collected by device 10 are filtered through a 0.45 micron or preferably 0.22 micron filter and the filtrate containing cell free nucleic acids is isolated and the nucleic acids therein are sequenced. In this manner, the sequencing sample is significantly enriched for cell free host nucleic acid relative to the much larger amount of nucleic acids present in intact host and microbial cells. The cell free nucleic acids are useful in the diagnostic and prognostic procedures disclosed elsewhere in this patent.

In a further embodiment, the nucleic acid originating from the host that is collected by device 10 is isolated from the nucleic acid originating from GI microbes prior to sequencing the collected host-originating nucleic acid.

In a further embodiment where multiple sites in the GI tract are sampled by device 10, or that multiple device 10 units are swallowed with each sampling a different region of the GI tract, a matrix is constructed of the putative sampling sites as determined by the position identification parameters disclosed above against the biomarker profile at each sampling location or position. Due to peristalsis of all luminal content in the caudal direction through the GI track, gastric cancer markers, for example, would be present in all samples collected between the stomach and the colon. Liver or pancreatic cancer markers, for example, would be present in the device 10 samples collected in the duodenal, jejunum, ileum and colon, but not in samples collected in the stomach. Colon cancer markers, for example, would be present only in a device 10 sample that was collected from the colon, with samples collected higher in the GI tract lacking these biomarkers. By way of an additional example, markers of inflammation are collected by one or more device 10 units at numerous spots along the GI tract and a region-specific GI tract inflammation map is created. In this manner, a matrix of sampling locations compared against a biomarker analysis can help identify the type of disease or malignancy as well as its location in the GI tract due to the unique multi-region sampling capabilities of device 10 and the non-homogenous content of the gastrointestinal lumen. When sampled and analyzed in the manner disclosed herein, GI fluids serve as a highly informative liquid biopsy that is able to both identify the type and anatomical location of a malignancy or disease.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms “a”, “an” and “the” are intended to include the plural forms as well, unless the context clearly indicates otherwise. It will be further understood that the terms “comprises” and/or “comprising,” when used in this specification, specify the presence of stated features, steps, operations, elements, and/or components, but do not preclude the presence or addition of one or more other features, steps, operations, elements, components, and/or groups thereof. As used herein, the term “and/or” includes any and all combinations of one or more of the associated listed items and may be abbreviated as “/”.

Spatially relative terms, such as “under”, “below”, “lower”, “over”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as “under” or “beneath” other elements or features would then be oriented “over” the other elements or features. Thus, the exemplary term “under” can encompass both an orientation of over and under. The device may be otherwise oriented (rotated 90 degrees or at other orientations) and the spatially relative descriptors used herein interpreted accordingly. Similarly, the terms “upwardly”, “downwardly”, “vertical”, “horizontal” and the like are used herein for the purpose of explanation only unless specifically indicated otherwise.

Although the terms “first” and “second” may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X” (e.g., where X is a numerical value) is also disclosed. It is also understood that the throughout the application, data is provided in a number of different formats, and that this data, represents endpoints and starting points, and ranges for any combination of the data points. For example, if a particular data point “10” and a particular data point “15” are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

I claim:

1. A method of identifying and/or localizing a pathology comprising:

sequentially collecting liquid samples from regions of the GI tract into a hollow tube by gradually expanding a radially collapsed hollow tube along a length thereof to thereby gradually pull gastrointestinal samples into said hollow tube and form a linear array of samples within said tube;

localizing each of said samples to a specific region of the GI tract; and characterizing cells and/or biomolecules in each of said samples and associating said cells and/or biomolecules with a pathology to a specific region of the GI tract to thereby identify and/or localize the pathology.

2. The method of claim 1, wherein said liquid samples are collected by one or more ingestible capsules configured for collection of a liquid sample in specific time ranges post gastric emptying.

3. The method of claim 1, wherein said liquid samples are collected by one or more ingestible capsules configured for collection of a liquid sample in specific pH ranges.

4. The method of claim 1, wherein localizing each of said samples to a specific region of the GI tract is carried out by identifying GI region-specific analytes in each of said liquid samples.

5. The method of claim 1, wherein said biomolecules are inflammation markers.

6. The method of claim 1, wherein said biomolecules are associated with epigenetic changes of DNA.

7. The method of claim 1, wherein said cells associated with the pathology include cancer cells.

8. The method of claim 1, wherein said cells associated with the pathology include immune cells.

9. The method of claim 1, wherein localizing the pathology to a specific region of the GI tract is carried out by identifying a GI region where a cell and/or biomolecule of interest first appears.

10. The method of claim 9, wherein said liquid samples are collected by one or more ingestible capsules configured for collection of a liquid sample in specific time ranges post gastric emptying.

11. The method of claim 9, wherein said liquid samples are collected by one or more ingestible capsules configured for collection of a liquid sample in specific pH ranges.

12. The method of claim 9, wherein said biomolecules are inflammation markers.

13. The method of claim 9, wherein said biomolecules are associated with epigenetic changes of DNA.

14. The method of claim 9, wherein said cells include cancer cells.

15. The method of claim 9, wherein said cells include immune cells.

16. The method of claim 3, wherein said liquid samples are collected by an ingestible capsule configured for sequential collection of said liquid samples.

17. The method of claim 11, wherein said liquid samples are collected by an ingestible capsule configured for sequential collection of said liquid samples.

18. The method of claim 1, wherein said hollow tube includes a closed distal end and an open proximal end.

19. The method of claim 1, wherein at least one liquid sample is collected from the small intestines.

* * * * *